US00RE35904E

United States Patent [19]

Paterson et al.

[11] E Patent Number: Re. 35,904

[45] Reissued Date of Patent: Sep. 22, 1998

[54] METHOD AND PROBES FOR DETECTING NUCLEOSIDE TRANSPORTER AND METHOD FOR PRODUCING THE PROBES

[75] Inventors: Alan R. P. Paterson; Carol E. Cass, both of Edmonton; Wendy P. Gati, Spruce Grove, all of Canada; John K. Buolamwini, Oxford, Miss.; Gary P. Jamieson, Melbourne, Australia; David P. McAdam, Melba, Australia; William A. Sawyer, Melbourne, Australia; James S. Wiley, Penrith, Australia; James D. Craik, Lennoxville, Canada; Morris J. Robins, Provo, Utah

[73] Assignee: Governors of the University of Alberta, Canada

[21] Appl. No.: 516,172

[22] Filed: Aug. 17, 1995

Related U.S. Patent Documents

Reissue of:

[64] Patent No.: 5,236,902
Issued: Aug. 17, 1993
Appl. No.: 617,714
Filed: Nov. 26, 1990

[51] Int. Cl.[6] ..... A61K 31/70; C07H 19/167; C07H 19/16; G01N 33/566

[52] U.S. Cl. ..... 514/24; 536/17.4; 536/18.5; 536/27.62; 436/501

[58] Field of Search ..... 536/17.4, 18.5, 536/27.62; 436/501; 514/24

[56] References Cited

PUBLICATIONS

F. Agbanyo et al., "5'-S(2-Aminoethyl)-N6-(4-Nitrobenzyl)-5'thioadenosine (SAENTA), A Novel Ligand With High Affinity for Polypeptides Associated With Nucleoside Transport", Biochem. J. 270: 605–614, Sep. 1990.

(List continued on next page.)

*Primary Examiner*—Rebecca E. Prouty
*Attorney, Agent, or Firm*—Bell Seltzer Intellectual Property Law Group of Alston & Bird, LLP

[57] ABSTRACT

The present invention is directed to compounds capable of binding to the es nucleoside transporter of animal cells having the general formula:

[

]

wherein n is 1–12; E is H, halogen, $NH_2$, OH, $OCH_3$, $O(CH_2)_nCH_3$ (where n is 1 to 12), SH, SR (where R is $CH_3$ or $(CH_2)_nCH_3$ and n is 1 to 12); A is HN, S, O, Se; X is N or C; Y is N or C; Z is N or C; $R_1$ is H or acyl; $R_2$ is C1 to C20 substituted or unsubstituted alkyl or heteroalkyl; substituted or unsubstituted aliphatic carbocycle or heterocycle; substituted or unsubstituted arene or heteroarene, aryl or substituted aryl; heteroaryl or substituted heteroaryl; $R_3$ is H, halogen, $NO_2$, $N_3$, SH, SR (where R is $CH_3$ or $(CH_2)_nCH_3$ and n is 1 to 12) *when Y is C and $R_3$ is absent when Y is N*; $R_4$ is H, OH [is] *or* halogen; $R_5$ is H, OH, halogen, $N_3$, acetal, hemiacetal; and $R_6$ is H, [—C=O—$HN_2$] —*CO—$NH_2$* or —C≡N when X is C and $R_6$ is [H] *absent* when X is N.

28 Claims, 8 Drawing Sheets

PUBLICATIONS

J.S. Wiley et al., "Cytosine Arabinoside Influx and Nucleoside Transport Sites in Acute Leukemia", J. Clin. Invest. 69: 479–489, Jan. 1982.

Gati, W. P. & Paterson, A.R.P. "Nucleoside Transport", *Red Blood Cell Membranes,* Agre, P. & Parker, J.C. (eds.) Marcel Dekker, New York (1989), pp. 635–661.

Wiley, J.S. et al., "Cyosine Arabinoside in the Treatment of T–Cell Acute Lymphoblastic Leukemia", *Australia & New Zealand Journal of Medicine,* 1987, 17:379–386.

Wiley, J.S. et al. "Nucleoside Transport in Acute Leukaemia and Lymphoma: Close Relation to Proliferative Rate", *British Journal of Haematology,* 1989, 71:203–207.

Gati, W.P. et al. "|$^{125}$I|Iodohydroxynitrobenzylthioinosine: a new high–affinity nucleoside transproter probe", *Biochemistry and Cell Biology,* 1987, 65:467–473.

Shohami, E. & Koren, R., "S–(N–Dansylaminoethyl)–6–mercaptoguanosine as a Fluorescent Probe for the Uridine Transport System in Human Erythrocytes", *Biochemical Journal,* 1979, 178:271–277.

Paterson, A.R.P. et al. "Inhibiton by Nitrobenzylthioinosine of Adenosine Uptake by Asynchronous HeLa Cells", *Molecular Pharmacology* 1977, 13:1147–1158.

Gati, W.P. et al., "Interaction of 2'–Halogeno–2'– deoxyuridines with the Human Erythrocyte Nucleoside Transport Mechanism", *Molecular Pharmacology,* 1983, 23:146–152.

Steck, T.L. & Kant, J.A. "Preparation of Impermeable Ghosts and Inside–out Vesicles From Human Erythrocyte Membranes", *Methods in Enzymology,* vol. 31, (Fleischer, S. & Packer, S. eds) Academic Press, New York, 1974 pp. 172–180.

Paul, B. et al., "Inhibitors of Nucleoside Transport, A Structure–Activity Study Using Human Erythrocytes", *Journal of Medicinal Chemistry,* 1975, 18:968–973.

Agbanyo, F.R. et al., "External Location of Sites on Pig Erythrocyte Membranes that Bind Nitrobenzylthioinosine", *Molecular Pharmacology,* 1988, 33:332–337.

Pande, S.V., "Liquid Scintillation Counting of Aqueous Samples Using Triton–Containing Scintillants", *Analytical Biochemistry,* 1976, 74:25–34.

Smith, P.K. et al., "Measurement of Protein Using Bicinchoninic Acid", *Analytical Biochemistry,* 1985, 150:76–85.

Bradley, et al., "Cell Lines Derived From a Human Myelomonocytic Leukaemia", *British Journal of Haematology,* 1982, 51:595–604.

Jamieson, G.P. et al., "Transport and Metabolism of 1–β–D–Arabinofuranosylcyosine in Human Ovarian Adenocarcinoma Cells", *Cancer Research,* 1989, 49:309–313.

Wiley et al., "Cytosine Arabinoside Influx and Nucleoside Transport Sites in Acute Leukemia", *Journal of Clinical Investigation,* 1982, 69:479–489.

Gati, W.P. & Paterson, A.R.P., "Interaction of |$^{3}$H|Dilazep at Nucleoside Transporter–Associated Binding Sites on S49 Mouse Lymphoma Cells", *Molecular Pharmacology,* 1989, 36: 134–141.

H. Hibasami et al. "Studies of Inhibition of Rat Spermidine Synthetase . . . " Biochem. J. 187: 419–428 (1980).

K. Samejima et al. "Achin of Decarboxylated S–Adenosjmethimine . . . " Arch. Biochem. Biophys. 201(1) 241–246 (Apr. 1980).

(a) NaH/$HOCH_2CH_2SH$/DMF. (b) (4–)$O_2NC_6H_4CH_2Br$/4A MOLECULAR SIEVES/DMF. (c) $NH_3$/MeOH. (d) $Ph_3P$/$EtO_2CN{=}NCO_2Et$/PHTHALIMIDE/THF. (e) $N_2H_4 \cdot H_2O$/EtOH/Δ. (f) DOWEX$_1$(Cl)/MeOH/$H_2O$.

METHOD AND PROBES FOR DETECTING NUCLEOSIDE TRANSPORTER AND METHOD FOR PRODUCING THE PROBES

Matter enclosed in heavy brackets [ ] appears in the original patent but forms no part of this reissue specification; matter printed in italics indicates the additions made by reissue.

FIELD OF INVENTION

This invention relates to methods and probes for the detection and measurement of nucleoside transport sites of animal cells.

BACKGROUND OF THE INVENTION

In animal cells, a number of transport processes mediate the passage of purine and pyrimidine nucleosides across the cell membrane (Gati and Paterson (1989), in "Red Blood Cell Membranes", Eds. Agre & Parker, pp. 635–661).

A major nucleoside transport activity in animal cells, including mammalian cells, is the equilibrative (facilitated diffusion) process mediated by a transporter of the plasma membrane which is highly sensitive to inhibition by derivatives of 9-β-D-ribofuranosyl-6-thiopurine such as nitrobenzyl thioinosine (NBMPR). The equilibrative, NBMPR-sensitive nucleoside transporter is referred to herein as the es nucleoside transporter.

The abundance of es nucleoside transporter sites is of significance in predicting the responsiveness of certain leukemias to nucleoside anti-metabolite therapy.

Analysis of equilibrium binding of $^3$H-NBMPR has been used to measure the abundance of nucleoside transporter sites in homogeneous populations of a variety of fresh and cultured human cells (Wiley et al. (1987) Aus. & N.Z. J. Med., vol. 17, pp. 379–386; Wiley et al. (1989), Br. J. Haematol. vol. 71, pp. 203–207).). Use of this tritiated ligand does not, however, permit identification of subpopulations of cells with different transporter densities in a heterogeneous cell population, such as usually occurs in human cancer. There are also serious practical limitations to clinical application of NBMPR equilibrium binding to estimating es nucleoside transporter abundance as the method is complex and time-consuming and requires large numbers of cells.

[$^{125}$I]Iodohydroxynitrobenzylthioinosine has been synthesised and used to label the es nucleoside transporter (Gati, Knaus, Wiebe, & Paterson (1987), Biochem. Cell. Biol. vol. 65, pp. 467–473). This iodinated nucleoside is not suitable for use in a clinical application because of high non-specific adsorption of the iodine-labelled nucleoside, the pH-dependence of its binding and the complexity of the assay procedure.

A fluorescent dansyl derivative of 6-thioquanosine has been synthesised and shown to bind to the es nucleoside transporter of human erythrocytes (Shohami & Koren, (1979), Biochem. J., vol. 178, pp. 271–277). The observed high non-specific binding of this derivative make it not as effective as desirable for the basis of a clinically useful technique. Dansyl derivatives also require excitation in the ultraviolet range (310 nm) and are poorly suited to use in flow cytometry techniques.

SUMMARY OF INVENTION

In accordance with one aspect of the invention compounds are provided capable of a compound capable of binding to the es nucleoside transporter of animal cells having the general formula:

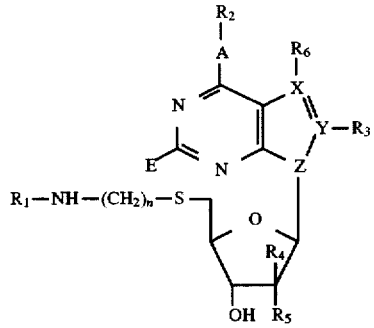

wherein n is 1–12; E is H, halogen, $NH_2$, OH, $OCH_3$, $O(CH_2)_nCH_3$ (where n is 1–12), SH, SR (where R is $CH_3$ or $(CH_2)_nCH_3$ and n is 1 to 12); A is NH, S, O, Se; X is N or C; Y is N or C; Z is N or C; $R_1$ is H or acyl; $R_2$ is C1 to C20 substituted or unsubstituted alkyl or heteroalkyl; substituted or unsubstituted aliphatic carbocycle or heterocycle; substituted or unsubstituted arene or heteroarene, aryl or substituted aryl; heteroaryl or substituted heteroaryl; $R_3$ is H, halogen, $NO_2$, $N_3$, SH, SR (where R is $CH_3$ or $(CH_2)_nCH_3$ and n is 1 to 12) *when Y is C and $R_3$ is absent when Y is N*; $R_4$ is H, OH or halogen; $R_5$ is H, OH, halogen, $N_3$, acetal, *or* hemiacetal; and $R_6$ is H, [—C=O—$NH_2$] —*CO*—*$NH_2$*, or —C≡N when X is C and $R_6$ is [H] *absent* when X is N.

In accordance with a further aspect of the invention, a process is provided for preparing a compound of the general formula:

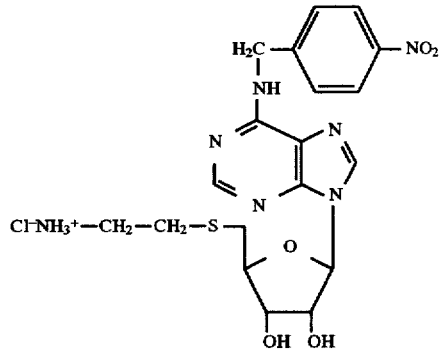

comprising the steps of:

(a) N'1 alkylation and rearrangement of 5'-S-(2-hydroxyethyl)-5'-thioadenosine to give 5'-S-(2-hydroxyethyl)-6-N-(4-nitrobenzyl)-5'-thioadenosine;

(b) treatment of the product of step (a) with diethylazodicarboxylate/triphenylphosphine followed by phthalimide to give 5'-S-(2-phthalimidoethyl)-$N^6$-(4-nitrobenzyl)-5'-thioadenosine;

(c) deprotection of the product of step (b) by heating with hydrazine in ethanol to give the phthaloyl hydrazide salt of 5'-S-(2-aminoethyl)-$N^6$-(4-nitrobenzyl)-5'-thioadenosine; and (d) conversion of the product of step (c) to 5'-S-(2-aminoethyl)-6-N-(4-nitrobenzyl)-5'-thioadenosine HCl by ion exchange chromatography on Dowex 1 ($Cl^-$) resin, i.e., styrene divinyl benzene resin.

In accordance with a further aspect of the invention, probes are provided capable of binding to the es nucleoside transporter of animal cells comprising a compound having the general formula:

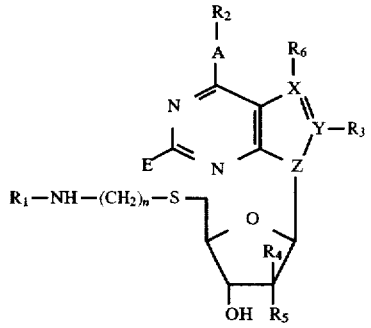

wherein n is 1–12; E is H, halogen, $NH_2$, OH, $OCH_3$, $O(CH_2)_nCH_3$ (where n is 1–12), SH, SR (where R is $CH_3$ or $(CH_2)_nCH_3$ and n is 1 to 12); A is NH, S, O, Se; X is N or C; Y is N or C; Z is N or C; $R_2$ is C1 to C20 substituted or unsubstituted alkyl or heteroalkyl; substituted or unsubstituted aliphatic carbocycle or heterocycle; substituted or unsubstituted arene or heteroarene, aryl or substituted aryl; heteroaryl or substituted heteroaryl; $R_3$ is H, halogen, $NO_2$, $N_3$, SH, SR (where R is $CH_3$ or $(CH_2)_nCH_3$ and n is 1 to 12) *when Y is C and $R_3$ is absent when Y is N*; $R_4$ is H, OH or halogen; $R_5$ is H, OH, halogen, $N_3$, acetal, *or* hemiacetal; and $R_6$ is H, [—C=O—$NH_2$] —*CO—$NH_2$*, or —C≡N when X is C and $R_6$ is [H] *absent* when X is N and $R_1$ is a reporter moiety or a reporter moiety and a linker moiety.

According to a further aspect of the invention, a method is provided of determining [as] *es* nucleoside transporter sites of animal cells comprising the steps of:

(a) contacting a suitable preparation of said cells with a probe in accordance with any of claims 5 to 16 to permit binding of said probe to said sites; and (b) determining said reporter moiety of said probe.

According to a further aspect of the invention, a [method is provided of determining a] pharmaceutical composition is provided in dosage unit form suitable for inhibiting es nucleoside transporter activity in animal cells and tissues comprising a compound in accordance with any of claims 1 to 3 or a pharmaceutically acceptable salt thereof in an amount effective to inhibit es nucleoside transporter activity in admixture with a suitable pharmaceutical carrier.

DETAILED DESCRIPTION OF THE INVENTION

The invention, as exemplified by preferred embodiments, is described with reference to the following drawings in which.

Figure 8A:
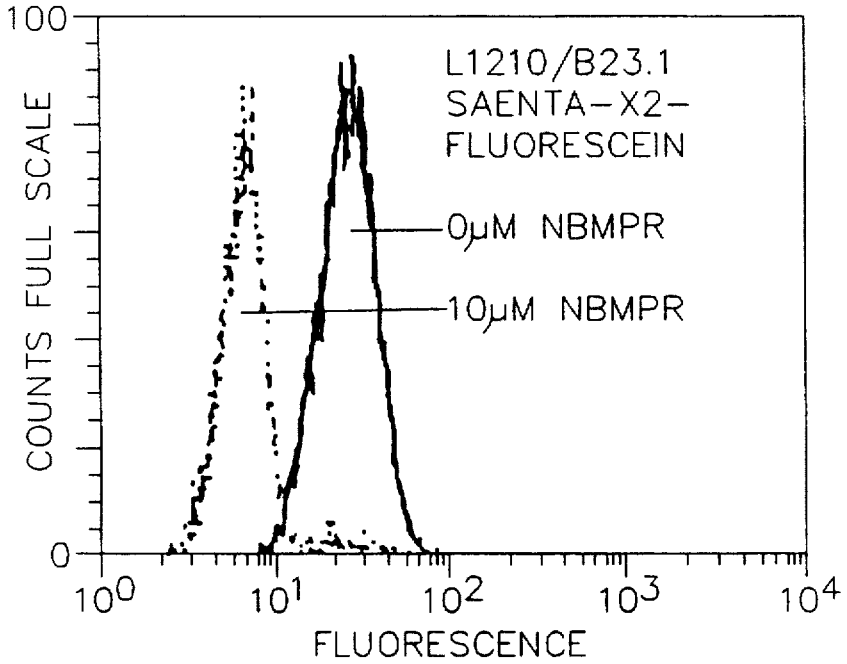

FIGS. 8A and B show selective staining of clonal cell lines by SAENTA-fluorescein probe.

FIGS. 9A–F show further data on selective staining by SAENTA-fluorescein probe.

The inventors have found that a novel group of nucleosides, 5'-S-(2 aminoethyl)-$N^6$(4-nitrobenzyl)-5'-thiadenosine(SAENTA) and derivatives and analogues thereof, have a high affinity for the es nucleoside transporter of human cells.

The direct synthetic route which would be expected to give the compound SAENTA i.e. treatment of $N^6$-(4-nitrobenzyl) adenosine (NBAdo) with thionyl chloride/HMPA to give the corresponding 5'-chloro-5'-deoxy-NBAdo followed by displacement of the 5'-chloro group with 2-aminoethanethiol/sodium hydride, or other thiol salts, was unsuccessful and resulted in decomposition involving loss of the 4-nitrobenzyl moiety from the 6-amino group of the adenine ring.

Nucleophilic displacement of the 5'-chloro group from 5'-chloro-5'deoxyadenosine with 2-aminoethanethiol/sodium hydride gave 5'-S-(2-aminoethyl)-5'-thioadenosine as expected. However the presence of the aliphatic primary amino function on this compound precluded direct alkylation of N1 of the adenine ring with 4-nitrobenzyl bromide. Projected sequences that involved amino protection and ultimate deprotection steps were cumbersome, and decomposition during the ultimate deprotection conditions again occurred.

This invention provides a novel process for synthesis of SAENTA which overcomes the problems described above. The process comprises the steps of displacement of the 5'-chloro group from 5'-chloro-5'-deoxyadenosine with 2-mercaptoethanol/sodium hydride, N1-alkylation with 4-nitrobenzyl bromide, rearrangement to the N6 isomer, conversion of the primary alcohol to give the 5-S-[(2-phthalimido)ethyl)-5'-thio compound, and deprotection to give the target 5'-S-(2-aminoethyl)-6-N-(4-nitrobenzyl)-5'-thioadenosine (SAENTA) salt.

Figure 1:
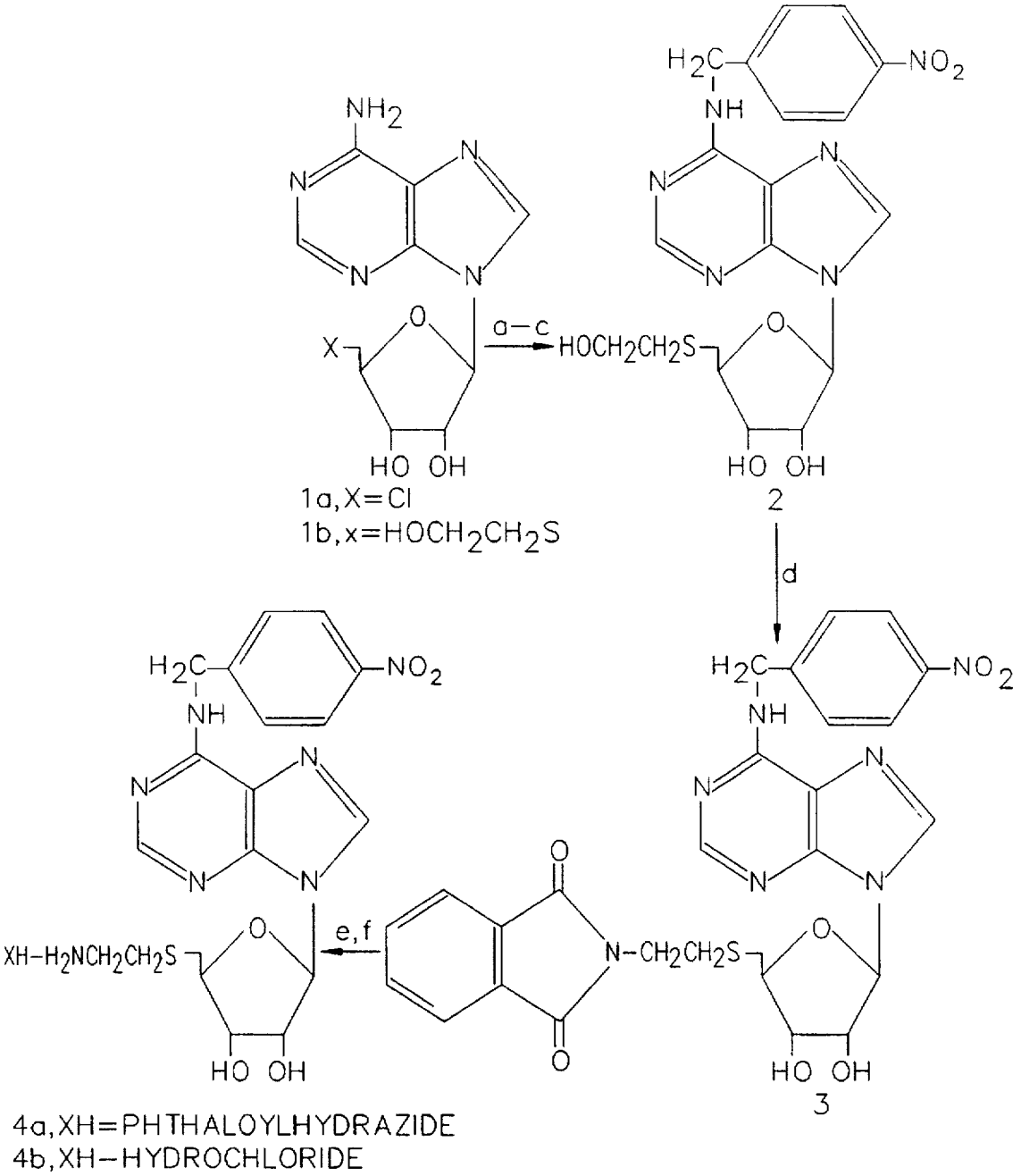
FIG. 1 shows a flow chart of the process for synthesising SAENTA.

The process of the invention is set out in schematic form in FIG. 1. The HCl salt of SAENTA is compound 4b of FIG. 1.

Previous studies of the es nucleoside transporter system (Paterson, Babb et al., (1977), Mol. Pharmacol., vol. 13, pp. 114; Gati, Knaus & Wiebe, (1983), Mol. Pharm., vol. 23, pp. 146–152) suggested that the sugar component of nucleosides was important for binding of a nucleoside to the es transporter site.

The inventors have found, surprisingly, that reporter moieties can be attached to the ribose ring of the novel SAENTA nucleosides without destruction of effective binding affinity for the es nucleoside transporter to provide novel probes for that transporter.

A "reporter" moiety, as that term is used herein, is a moiety forming part of a probe which permits detection and determination of the probe and hence of the es nucleoside transporter to which the probe is bound. A reporter moiety may permit such detection and determination either by itself emitting a detectable signal or by virtue of having an affinity for a reporter-specific moiety which is detectable.

Reporter moieties are attached to SAENTA or one of its analogs either directly or through a linker moiety. A reporter moiety is "attached" to a linker moiety or to a nucleoside, as the term "attached" is used herein, when they are attached in such a manner as to resist separation under normal physiological conditions. It is presently preferred that the reporter moiety of a probe of the invention is attached to the nucleoside portion of the probe covalently through a linker moiety selected from the group —CO—; —NHCS—; —NHCO$(CH_2)_5$CO— or 2-amino-5-(3-chlorotriazinyl)-.

One may however employ any suitable linker moiety which does not result in loss of binding of the probe to the es nucleoside transporter to an unacceptable degree.

It is preferred that a probe of the invention has a binding affinity for the es nucleoside transporter of Kd or [$K_1$] $K_i$ < about $5\times10^{-8}$M.

The SAENTA or other nucleoside portion of the novel probes of the invention enables them to bind specifically to the es transporter and the bound probe is determined by recognition and determination of the reporter moiety.

The novel nucleosides of the invention have also been attached to macromolecular carriers such as agarose gel to provide a device for isolation of the es nucleoside transporter.

In a preferred embodiment of the invention, reporter moieties of probes are moieties which themselves emit a detectable signal, such as moieties which are fluorescent or radioactive. The es nucleoside transporter sites of cells are determined by determining the signal emitted by the reporter moiety after binding of the probe to the transporter. Any suitable moiety which produces a detectable signal may be used as reporter moiety.

Suitable fluorescent materials for use as reporter moieties include fluoresceins, rhodamines, coumarin derivatives, Cascade Blue*, Texas red*, Bodipy*, erythrosin, eosin, NBD, fluorescent phycobiliproteins and their conjugates and fluoresceinated microbeads.

Use of fluors such as the phycobiliproteins and fluoresceinated microbeads will permit amplification of the fluorescent signal where cells have few es transporter sites. Dyes including luminescent groups may also be used as reporter moieties, as well as magnetisable groups such as gadolinium complexes and electron-opaque groups.

In a further embodiment of the invention, the reporter moiety of a probe is determined after its interaction with a reporter-specific moiety which is capable of recognising and complexing to the reporter moiety.

Es nucleoside transporter sites on mammalian cells are determined by contacting the cells with the probe to permit binding of the probe to the transporter, followed by contacting the treated cells with a reporter-specific moiety which binds specifically to the particular reporter moiety of the probe. The es nucleoside transporters are determined by determining the reporter-specific moieties by a suitable technique after binding of the probe to the transporter. Examples of suitable reporter moiety/reporter-specific moiety binding pairs include avidin/biotin, avidin/iminobiotin, streptavidin/biotin and antigen/antibody pairs such as fluorescein/antifluorescein antibody.

For example, the primary amino group of SAENTA may be biotinylated and the biotin reporter moiety detected and measured interaction with commercially available fluorescent derivatives of avidin or streptavidin which are determined by suitable methods.

Where the reporter-specific moiety is an antibody, its determination may be by standard second antibody or ELISA methods.

Reagents for carrying out the method of the invention for determination of es nucleoside transporter sites can be formulated in kits. The kits would comprise, in part, a desired probe, a reporter-specific moiety specific for the reporter moiety of the probe and means for determining the reporter-specific moiety. If the reporter moiety of the probe itself emits a detectable signal, the kit need not include a reporter-specific moiety and means for its determination.

In a further embodiment of the invention, the reporter moiety of a probe is radioactive and determination of its binding to the es transporter is by measurement of the emitted radiation. Examples of suitable radioactive reporter moieties are moieties labelled with γ-emitters such as $^{125}$I, $^{123}$I and $^{99m}$Tc, for example, $^{125}$I-labelled tyrosine in polythrosine.

In a further embodiment, SAENTA or an analogue is labelled with a radioactive label, for example $^{125}$I or $^{3}$H to provide a probe for determination of the es transporter.

Radioactively-labelled derivatives of SAENTA or its analogues have application in the external non-invasive imaging of body tissues, especially those having high levels of es transporter sites such as lung and vascular endothelium.

The nucleosides of the invention such as SAENTA inhibit es nucleoside transporter activity by binding strongly to the transporter. These nucleosides provide pharmaceutical agents suitable for inhibiting es nucleoside transporter activity in animal cells and tissues, including human cells and tissues. They may be mixed with a suitable pharmaceutical carrier to provide novel pharmaceutical compositions for use in administration to [a] an animal to inhibit es transporter nucleoside activity.

EXAMPLE 1

Synthesis and characterisation of SAENTA

General: All spectra were determined on commercial instruments using established techniques. $^{1}$H NMR spectra were determined at 400 MHz and $^{13}$C NMR spectra at 75.5 MHz with $Me_4Si$ as internal standard in the solvents noted. Melting points were determined on a hot-stage apparatus and are incorrected. Ultraviolet extinction values are in units of $M^{-1}cm^{-1}$.

The process used to synthesise SAENTA is set out schematically in FIG. 1.

5'-S-(2-Hydroxyethyl)-5'-thioadenosine (1b). To a mixture of sodium hydride (1.5 g, 50% dispersion in oil, 31 mmol) in DMF (40 mL) was added 2-thioethanol (1.65 mL, 1.84 g, 24 mmol) dropwise, and the mixture was stirred under argon for 15 min at ambient temperature. 5'Chloro-5'-deoxyadenosine (1a) (4.3 g, 15 mmol) was added portion wise and stirring was continued overnight. The mixture was concentrated under reduced pressure and subjected to flash chromatography (MeOH/$CHCl_3$, 3:7) to give the triol (1b) as a white solid (3.23 g, 66%) that was crystallized from EtOH to give colourless crystals of 1b with mp 198°–201° C.; UV (MeOH) max 259 nm (ε 15 900 ); $^{1}$H NMR ($Me_2SO$-$d_6$) δ 8.36 (s, 1, H8), 8.16 (s, 1, H2), 7.29 (br s, 2, $NH_2$), 5.89 (d, $J_{1'-2'}$=5.9 Hz, 1, H1'), 5.49 (d, $J_{OH-2'}$=6.0 Hz, 1, OH2'), 5.31 (d, $J_{OH-3'}$=5.0 Hz, 1, OH3'), 4.76 (t, J=5.5 Hz, 1, $CH_2OH$), 4.75 ("q", $J_{2'-3'}$=5.5 Hz, 1, H2'), 4.18 ("q", $J_{3'-4'}$=4.8 Hz, 1, H3'), 4.02 (m, $J_{4'-5'a}$=6.0 Hz, $J_{4'-5'b}$=6.8 Hz, 1, H4'), 3.52 ("q", J=6.5 Hz, 2, $CH_2OH$), 2.96 (m, $J_{5'a-5'b}$=14.0 Hz, 1, H5'a), 2.85 (m, 1, H5'b), 2.60 (t, 2, $SCH_2$); $^{13}$C NMR ($Me_2SO$-$d_6$) δ 155.97 (C6), 152.57 (C2), 149.36 (C4), 139.76 (C8), 119.06 (C5), 87.28 (C1'), 83.69 (C4'), 72.60, 72.44 (C3',3'), 60.76 ($CH_2OH$), 34.55 (C5'), 34.19 ($SCH_2$): MS m/z 327.0994 (M+=327.1001). Anal. Calcd for $C_{12}H_{17}N_5O_4S$ (327.4): C, 44.03; H, 5.23; N, 21.39; S, 9.79. Found: C, 43.91; H, 5.16; N, 21.52; S, 9.77.

5'-S-(2-Hydroxyethyl)-6-N-(4-nitrobenzyl)-5'-thioadenosine (2). A mixture of triol 1b (650 mg, 2.0 mmol), 4-nitrobenzyl bromide (2.16 g, 10 mmol), and powdered 4A molecular sieves (2.0 g) in dry DMF (15 mL was stirred for 4 days in a stoppered flask at ambient temperature, and filtered. The filtrate was concentrated under reduced pressure and the resulting crystalline mass was triturated with acetone (3×) and toluene (3×). The solid residue was dissolved in MeOH (10 mL) and treated with $NH_3$/MeOH (10 mL; w/v, 1:1, prepared at −10° C.). This solution was stirred for 5 h at ambient temperature and concentrated to a red gum. The gum was dissolved in hot MeOH and cooled to give a brown solid that was recrystallized from MeOH to give title compound 2 as red needles (360 mg, 39%). The mother liquors were concentrated and the residue subjected to flash chromatography (MeOH/$CHCl_3$, 2:23) to give a red solid that was recrystallized to give further red needles (165 mg, 19%) of 2 (total 57%) with mp 157°–158° C.; UV (MeOH) max 270 nm (ε 24 700), HCl/MeOH) max 274 nm (ε 29 900), (NaOH/MeOH) max 271 nm (ε 24 500); $^1$H NMR ($Me_2SO$-$d_6$) δ 8.62 (br s, 1, NH), 8.46 (s, 1, H8), 8.26 (s, 1, H2), 8.20 (d, $J_{AB}$=8.8 Hz, 2, Ar), (d, 2, Ar), 5.96 (d, $J_{1'-2'}$=5.7 Hz, 1, H1'), 5.56 (d, $J_{OH-2'}$=5.8 Hz, 1, OH2'), 5.39 (d, $J_{OH-3'}$=5.0 Hz, 1, OH3'), 4.85 (br s, 2, $CH_2Ar$), 4.81 (t, $J_{2'-3'}$=5.4 Hz, 1, H2'), 4.18 (br q, $J_{3'-4'}$=4.0 Hz, 1, H3'), 4.05 (m, $J_{4'-5'a}$=6.0 Hz, $J_{4'-5'b}$=7.2 Hz, 1, H4'), 3.54 (dt, J=5.5 Hz, 2, $CH_2OH$2.97 (m, $J_{5'a-5'b}$=13.8 Hz, 1, H5'a), 2.87 (m, 1, H5'b), 2.62 (t, 2, $SCH_2$); $^{13}$C NMR ($Me_2SO$-$d_6$) δ 154.32 (C6), 152.56 (C2), 149.31 (Ar), 148.26 (C4), 146.35 (Ar), 140.13 (C8), 128.01 (Ar), 123.44 (Ar), 120.01 (C5), 87.44 (C1'), 84.04 (C4'), 72.71, 72.54 (C2',3'), 60.85 ($CH_2OH$), 43.31 ($CH_2Ar$), 34.63 (C5'), 34.30 ($SCH_2$); MS m/z 417.0969 [$C_{17}H_{17}N_6O_5S$ ($MC_2H_5O$)=417.0981]. Anal. Calcd for $C_{19}H_{22}N_6O_6S$ (462.5): C, 49.34; H, 4.79; N, 18.17. Found: c, 48.99; H, 4.70; N, 18.04

6-N-(4-Nitrobenzyl)-5'-S-[2-phthalimido)ethyl]-5'-thioadenosine (3). Diethylazidocarboxylate (475 μL, 525 mg, 3.0 mmol) was added slowly at ambient temperature to a mixture of triphenylphosphine (525 mg, 2.0 mmol) and triol 2 (460 mg, 1.0 mmol) in dry THF (20 mL) and the mixture was stirred for 15 min to give a clear solution. Phthalimide (450 mg, 3.1 mmol) was added and the solution stirred overnight. Evaporation of the reaction mixture followed by flash chromatography (MeOH/$CHCl_3$, 7:93) of the residue gave the protected amine (3) as a white solid (440 mg, 73%) that was crystallized from $CH_2Cl_2$/hexanes to give crystals with mp 108°–109° C.; UV (MeOH) max 239, 271 nm (ε 8600, 12 900); $^1$H NMR ($CDCl_3$) δ 8.30 (br s, 1, H8), 8.14 (d, $J_{AB}$=8.8 Hz, 2, Ar), 8.02 (s, 1, H2), 7.83, 7.73 (m, m; 2, 2; Ar'), 7.56 (d, 2, Ar), 5.99 (d, $J_{1'-2'}$=4.5 Hz, 1, H1'), 5.26 (d, $J_{OH-2'}$=4.8 Hz, 1, OH2'), 4.98 (br, 2, CH2Ar), 4.75 (d, $J_{OH-3'}$=5.1 Hz, 1, OH3'), 4.71 (br q, $J_{2'-3'}$=4.6 Hz, 1, H2'), 4.37 (br q, $J_{3'-4'}$=5.0 Hz, 1, H3'), 4.26 (m, $J_{4'-5'a}$=5.2 Hz, $J_{4'-5'b}$=5.0 Hz, 1, H4'), 3.86 (t J=7.0 Hz, 2, $CH_2NPhth$), 3.01 (m, $J_{5'a-5'b}$=13.8 Hz, 1, H5'a), 2.96 (m, 1, H5'b), 2.88 (m, 2, $SCH_2$); $^{13}$C NMR ($CDCl_3$) δ 167.54 (Ar'), 154.19 (c6), 152.38 (C2), 149.11 (Ar), 146.85 (C4), 146.50 (Ar), 138.63 (C8), 133.63, 131.42 (Ar'), 127.66, 123.12 (Ar), 122.61 (Ar'), 119.68 (C5), 88.68, (C1'), 83.61 (C4') 73.59, 72.26 (C2',3'), 43.01 (C $H_2Ar$), 36.36 ($CH_2NPhth$), 33.46 (C5'), 30.28 ($SCH_2$),; MS (FAB) m/z 592 (M+1). Anal. Calcd for $C_{27}H_{25}N_7O_7S.0.5H_2O$ (600.6): C, 53.99; H, 4.36; N, 16.32. Found: C, 53.87; H, 4.24; N, 16.21.

5'-S-(2-Aminoethyl)-6-N-(4-nitrobenzyl)-5'-thioadenosine (SAENTA) phthaloylhydrazide (4a). To a solution of 3 (250 mg, 0.42 mmol) in EtOH (10 mL) was added $N_2H_4.H_2O$ (150 μL, 155 mg, 3.0 mmol) and the mixture was heated at reflux for 12 h. EtOH (15 mL) was added, the clear solution was filtered, and the filtrate cooled. The solid that separated was recrystallized from EtOH to give the title salt (4a) as pale yellow plates (116 mg, 43%) with mp 115°–117° C.; UV (MeOH) max 272 nm (ε 26 900), (0.1N HCl/MeOH) max 273 nm (ε 30 500), 0.1N NaOH/MeOH) max 271 nm (ε 30 300); $^1$H NMR ($Me_2SO$-$d_6$/$D_2O$) δ 8.52 (s, 1, H8), 8.33 (s, 1, H2), 8.20 (d, $J_{AB}$=8.7 Hz, 2, Ar), 8.15, 7.88 (m, M; 2, 2; Ar'), 7.62 (d, 2, Ar), 5.95 (d, $J_{1'-2'}$=6.0 Hz, 1, H1'), 4.85 (br s, 2, $CH_2Ar$), 4.76 (dd, $J_{2'-3'}$=4.0 Hz, 1, H2'), 4.21 (dd, $J_{3'-4'}$=4.0 Hz, 1, H3'), 4.04 (m, 1, H4'), 2.92 (m, 4, H5'a,5'b,$CH_2ND_2$), 2.72(t, 7.0 Hz, 2, $SCH_2$); $^{13}$C NMR ($Me_2SO$-$d_6$/$D_2O$) δ 157.29 (Ar'), 154.84 (C6), 153.28 (C2), 149.38, 148.52 (Ar), 147.03 (C4), 140.78 (C8), 132.90 (Ar'), 128.75 (Ar), 128.66, 126.08 (Ar'), 124.11 (Ar), 120.01 (C5), 88.15 (C1'), 84.20 (C4'), 73.26, 72.96 (C2',3'), 43.28 ($CH_2Ar$), 34.26 (C5'), 30.97 ($SCH_2$); MS (FAB) m/z 462 [M+1 (nucleoside cation)], 162 (phthaloylhydrazide anion+1). Anal. Calcd for $C_{27}H_{29}N_9O_7S.H_2O$ (641.7): C, 50.54; H, 4.85; N, 19.65. Found: C, 50.12; H, 4.54; N, 19.47.

5'-S-(2-Aminoethyl)-6-N-(4-nitrobenzyl)-5'-thioadenosine (SAENTA) hydrochloride (4b). A solution of 4a in 50% MeOH/$H_2O$ was acidified with a few drops of HOAc and applied to a column of Dowex 1 ($Cl^-$) anion exchange resin (prewashed with 0.1M NaCl/$H_2O$ and equilibrated with 50% MeOH/$H_2O$). The column was eluted with 50% MeOH/$H_2O$ and then MeOH. Combined fractions containing 4b were concentrated to give the stock solution (stored at −20° C.) of 4b ($\epsilon_{272\ nm}$=2.7×10$^4$M$^{-1}$cm$^{-1}$).

EXAMPLE 2

Inhibition of NBMPR binding by SAENTA and acetyl SAENTA

Blood from adult domestic pigs (Gainers, Edmonton, Alberta, Canada) was collected into 0.2 vol. of anticoagulant solution (90 mM-sodium citrate/16 mM-citric acid/16 mM-monosodium phosphate/2 mM-adenine/12 mM-inosine) and immediately processed by conventional methods for recovery of erythrocytes.

Unsealed ghosts were prepared at 4° C. by the procedure of Steck & Kant, (1974), Methods in Enzymology, vol. 31, pp. 172–180, modified by the inclusion of 0.1 mM phenylmethane sulphonyl fluoride, and stored at −70° C.

NBMPR was prepared as described by Paul, Chen & Paterson (1975), J. Med Chem., vol. 18, pp. 968–973. [G-$^3$H]NBMPR (23 Ci/mmol), obtained from Moravek Biochemicals, Brea, CA., U.S.A., was purified by using a Spheri-10 RP18 100 mm×4.6 mm column (Brownlee Labs, Santa Clara, CA., U.S.A.), eluted with a methanol/water gradient.

Site-specific binding of [$^3$H]NBMPR

Binding to unsealed ghosts was determined by a filtration assay, as described by Agbanyo, Cass & Paterson (1988) Mol. Pharmacol., vol. 33, pp. 332–337. Assay mixtures (final volume, 1.2 ml; two samples per condition) contained 2 nM-[$^3$H]NBMPR, graded concentrations of test compound and unsealed ghosts (10 μg of protein/ml) in 5 mM-sodium phosphate buffer, pH 7.4, at 22° C., and, for determination of non-specific binding, 5 μM non-radioactive NBMPR was present. After a 20 min incubation at 22° C., membrane material from 1 ml portions of assay mixtures was collected by vacuum filtration on Whatman GF/C microfibre filters, which were then rapidly washed three times with 2 ml portions of ice-cold 5 mM-sodium phosphate buffer. The filters were placed in scintillation vials and assayed for radioactivity after a 16 h incubation in 8 ml of Triton X-100-based scintillation fluid as described by Pande (1976) Anal. Biochem., vol. 74, pp. 25–34. Protein was determined by the bicinchoninic acid method of Smith et al. (1985) Anal. Biochem., vol. 150, pp. 76–85.

Correction for non-specific binding was determined by performing the assay in the presence of 5 μM-non radioactive NBMPR. Replicate mixtures contained ghosts, 2 nM-[$^3$H]NBMPR, graded concentrations of SAENTA or acetyl SAENTA (prepared as in Example 1) and, in mixtures used for non-specific binding, 5 μM-non radioactive NBMPR. Values for [$^3$H]NBMPR specifically bound in the presence of inhibitor are expressed as percentages of that bound in its absence.

$IC_{50}$ values were determined from plots of % site-bound NBMPR in presence of test compound against concentration of test compound.

SAENTA was found to have an $IC_{50}$ value of 330 nM and the value for acetyl SAENTA was 76 nM. Both compounds showed strong inhibition of NBMPR binding to the nucleoside transporter, indicating a high affinity of binding to the es nucleoside transporter.

EXAMPLE 3

SAENTA—fluorescein probes; synthesis and characterisation

A group of SAENTA—fluorescein probes have been synthesised as set out in Table 1. Fluorescein was linked either at the 5 or 6 position and a variety of linker moieties, designated X1, X2, X4 and X8 as identified in Table 1 were used to link the fluorescein reporter moiety to SAENTA.

Figure 2:
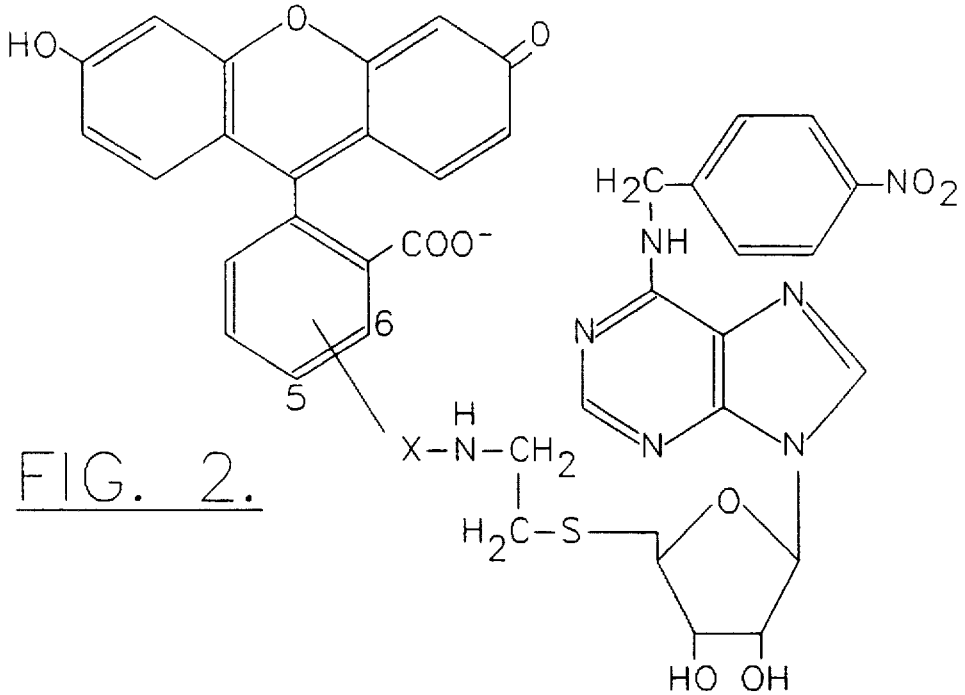
FIG. 2 shows the chemical structure of SAENTA-fluorescein probes in accordance with the invention.

The structure of the probes is shown in FIG. 2.

TABLE 1

| Linkage (X) | Fluorescein position | No. of atoms in linkage | Name |
|---|---|---|---|
| —CO— | 5 | 1 | 5-(SAENTA-X1-)fluorescein |
| —CO— | 6 | 1 | 6-(SAENTA-X1)-fluorescein |
| —NHCS— | 5 | 2 | 5-(SAENTA-X2)-fluorescein |
| —NHCS— | 6 | 2 | 6-(SAENTA-X2)-fluorescein |
| 2-Amino-5-(3-chloro-triazinyl) | 5 | 4 | 5-(SAENTA-X4)-fluorescein |
| —NHCO$(CH_2)_5$CO— | 5 | 8 | 5-(SAENTA-X8)-fluorescein |
| —NHCO$(CH_2)_5$CO— | 6 | 8 | 6-(SAENTA-X8)-fluorescein |

Synthesis (i) SAENTA phthalhydrazide salt prepared as described in Example 1, was reacted with amine-reactive fluorescein derivatives (5- or 6-isothiocyanate, succinimidyl carboxylic acid ester or the 5-dichlorotriazinyl derivatives of fluorescein) as in procedure described below which yielded 6-(SAENTA-X2)-fluorescein. Preliminary purification of the synthetic products was done by TLC. The TLC purified products which were single compounds or a mixture of 5- and 6-isomers were further purified by HPLC which was used to resolve the mixtures of 5- and 6-isomers into single products.

(ii) 6-(SAENTA-X2)-Fluorescein was prepared by heating fluorescein-6-isothiocyanate (7.8 mg, 0.2 mmol) with SAENTA phthalhydrazide salt (6.2 mg, 0.1 mmol) in methanol in the presence of $Et_3N$ (5.0 μl, 5.0 mg, 0.5 mmol) at 37° C. in the dark for 2 hr. The reaction mixture was concentrated under reduced pressure at 30° C. and the residue chromatographed over silica gel (TLC, 20×20 cm plates, 2.0 mm layer thickness) using acetonitrile: aqueous ammonium chloride/bicarbonate (0.05M), 4:1 v/v as development solvent. The band at Rf 0.8 was extracted in methanol, concentrated and purified by HPLC (Whatman Partisil 10 ODS-3 reversed phase (0.9×25 cm) column ($C_{18}$) eluted with 10 mM phosphate buffer: MeOH, 65:35 v/v, 40° C. (isocratically at 2 ml/min, Rt 22 min) to obtain 5'-S-[2-fluorescein-6-thioureidyl)ethyl]-$N^6$-(4-nitrobenzyl)-5'-thioadenosine (6-(SAENTA-X2-)-fluorescein), 5.1 mg, 60%. The UV spectrum (FIG. 3) exhibited maxima at 242, 272 and 498 nm with a molar absorption coefficient of $63.0\times10^3$ at 498 nm in 10 nM phosphate buffer: MeOH 65:35 v/v, pH 7.6. Fast atom bombardment mass spectrum (FABMS) calcd for $C_{40}H_{34}N_8O_{10}S_2$: 850; FOUND 851 (M+1).

Similarly prepared were:

(iii) 5'-S-[2-(Fluorescein-5-thioureidyl)ethyl]-$N^6$-(4-nitrobenzyl)-5'-thioadenosine 5-(SAENTA-X2)-fluorescein, 90%), FABMS calcd for $C_{40}H_{34}N_8O_{10}S_2$: 850; found: 851 (M+1);

(iv) 5'-S-[2-(6-(Fluorescein-5-carboxamido) hexanoylamino)ethyl]-$N^6$-(4-nitrobenzyl)-5'-thioadenosine(5-(SAENTA-X8)-fluorescein, 85%), FABMS calcd for $C_{46}H_{44}N_8O_{12}S$: 932; found: 933 (M+1);

(v) 5'-S-[2-(6-(Fluorescein-6-carboxamido)hexanoylamino) ethyl]-$N^6$-(4-nitrobenzyl)-5'-thioadenosine(6-(SAENTA-X8)-fluorescein, 80%), FABMS calcd for $C_{46}H_{44}N_8O_{12}S$: 932; found: 933 (M+1);

(vi) 5'-S-[2-(6-(Fluorescein-5-carboxamido)ethyl]-$N^6$-(4-nitrobenzyl)-5'-thioadenosine(5-(SAENTA-X1)-fluorescein, 54%), FABMS calcd for $C_{40}H_{33}N_7O_{11}S$: 819; found: 820 (M+1);

(vii) 5'-S-[2-(6-(Fluorescein-6-carboxamido)ethyl]-$N^6$-(4-nitrobenzyl)-5'-thioadenosine(6-(SAENTA-X1)-fluorescin, 55%), FABMS calcd for $C_{40}H_{33}N_7O_{11}S$: 819; found: 820 (M+1);

(viii) The Rf values (TLC), retention times (HPLC) and chromatographic conditions used for separating the latter compounds are presented in Table 2.

(ix) The 5- and 6-isomers were distinguished by their $^1$H NMR spectra. In DMSO-$d_6$, containing tetramethylsilane as an internal standard, the fluorescein H-7 proton signal appears as a doublet around δ 7.2 (J=10 Hz) for the 5-isomers, whereas for the 6-isomers this signal appears as a singlet around δ 7.7.

TABLE 2

| Name | % Yield | TLC $R_f$[a] | HPLC RT (min) | FAB-MS[b] Calcd. | FAB-MS[b] Found |
|---|---|---|---|---|---|
| 5-(SAENTA-X1)-fluorescein | 55 | 0.62 | 14[c] | 819 | 820 (M + 1) |
| 6-(SAENTA-X1)-fluorescein | 54 | 0.62 | 10[c] | 819 | 820 (M + 1) |
| 5-(SAENTA-X2)-fluorescein | 90 | 0.74 | 33[c] | 850 | 851 (M + 1) |
| 6-(SAENTA-X2)-fluorescein | 65 | 0.80 | 22[c] | 850 | 851 (M + 1) |
| 5-(SAENTA-X4)-fluorescein | 50 | 0.82 | 45[c] | | |
| 5-(SAENTA-X8)-fluorescein | 85 | 0.68 | 36[d] | 932 | 933 (M + 1) |
| 6-(SAENTA-X8)-fluorescein | 80 | 0.68 | 29[d] | 932 | 933 (M + 1) |

Figure 3:
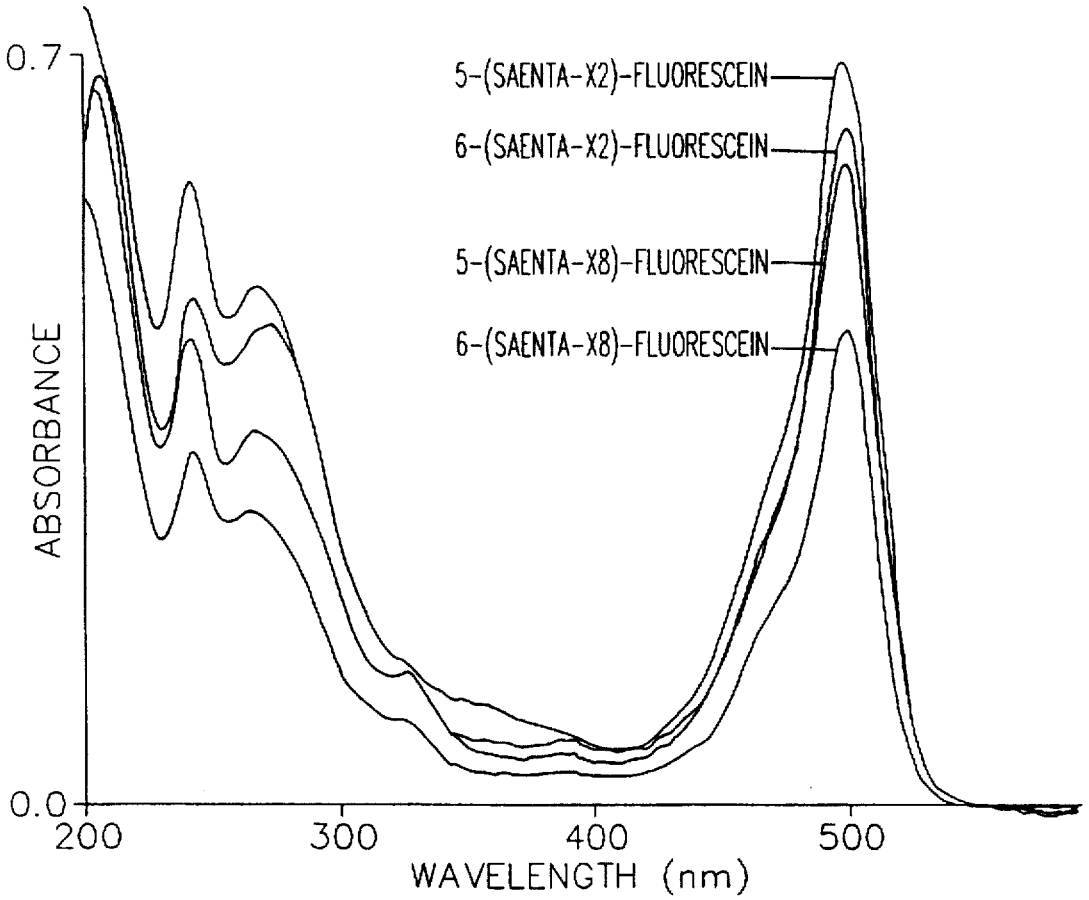
FIG. 3 shows the UV absorption spectrum of SAENTA-fluorescein probes.

[a]TLC over silica gel, developed in acetonitrile: aqueous 50 mM ammonium chloride/bicarbonate, 4:1
[b]Fast atom bombardment mass spectrometry (FAB-MS) was done in the +ve mode, in Cleland matrix
[c]Whatman Partisil 10 ODS-3 reversed phase ($C_{18}$) column (9.4 mm × 250 mm), eluted with 10 mM phosphate buffer (pH 7.4): MeOH, [63.]65:35 (isocratic, 2 ml/min)
[d]Dynamax-300A reversed phase ($C_{18}$) column (21.4 mm × 250 mm), 10 mM phosphate buffer (pH 7.4): MeOH, 60[.]:40 (solvent A); MeOH (solvent B). Gradient elution (7 ml/min); initial 100% A; 5 min, 90% A:10% B; 20 min, 85% A:15% B; 45 min, 85% A:15% B The UV spectra of the SAENTA-fluorescein probes are shown in FIG. 3. Spectra were recorded with a Hitachi 3200 Spectrophotometer at 25° C. in phosphate buffer/MeOH (65:35) solution pH 7.6, at sample concentrations of 7.5, 6.2, 5.9 and 4.9 μM, for 5-(SAENTA-X2)-, 6-(SAENTA-X2)-, 5-(SAENTA-X2)-, and 6-(SAENTA-X8)-fluorescein, respectively.

Those skilled in the art will appreciate that SAENTA-fluorescein probes may be prepared by other synthetic routes, for example by coupling using carbodiimides.

EXAMPLE 4

Binding of SAENTA-fluroscein probes to the nucleoside transporter

Materials

[$^3$H]NBMPR from Moravek Biochemicals Brea, CA, U.S.A. was purified by reverse phase HPLC using methanol-water as solvent. Unlabelled NBMPR was supplied by Sigma (St. Louis, MO, U.S.A.). [$^3$H]Cytosine arabinoside (araC) and [$^{14}$C]polyethylene glycol were obtained from Amersham, Buckinghamshire, England. Dilazep was a gift from Roche, Dee Why, Australia. Incubations were carried out using imidazole-buffered saline (IBS; 145 nM NaCl, 5 mM KCl, 5 mM imidazole-Cl, 1 mM $MgCl_2$ and 5 mM glucose, pH 7.4).

Cell Culture

The human leukaemic cell line RC2a, of myelomonocytic origin (Bradley et al., 1982 Brit. J. Haematol., vol. 51, pp. 595–604) was maintained in RPMI 1640 medium containing 10% foetal calf serum, 2 mM glutamine, 20 mM HEPES (pH 7.4) (Flow Laboratories, Sydney, Australia) and 20 mg/l gentamycin sulphate (Roussell, Castle Hill, Australia). Cell densities were maintained below $5\times10^5$/ml. Cells were collected by centrifugation and resuspended in buffered saline for assays.

(a) Inhibition of [$^3$H]Cytosine arabinoside (araC) Influx by [SAENTA -$X_2$- fluorescein] *SAENTA-X2-fluorescein*

Prior to measurement of [$^3$H]araC uptake, RC2a leukaemic cells were treated at 20° C. for 10 min with Prior to measurement of [$^3$H]araC uptake, RC2a leukaemic cells were treated at 20° C. for 10 min with graded concentrations (0–0.05 μM) of [SAENTA-$x_2$-fluorescein] *SAENTA-X2-fluorescein* prepared as in Example 3. Treated cells (100 μl, $5\times10^7$ cells/ml) were added to [$^3$H]araC (100 μl) in IBS medium in 1.5 ml centrifuge tubes to give a final araC concentration of 50 μM. [$^3$H]araC uptake was ended 20 sec. later by the addition of 800 μl of ice-cold dilazep (750 μM) (Jamieson et al., 1989). Phthalate oil was added immediately and the tube spun at 8000 g for 2 min. Medium above the oil was aspirated, the tube walls washed, and the oil above the cell pellet removed. Pellets were solubilized using 0.5M NaOH and the [$^3$H]araC contents were measured by liquid scintillation counting. The effectiveness of dilazep in stopping influx was confirmed by adding dilazep to cells prior to the addition of [$^3$H]araC. The uptake of araC was corrected for extracellular [$^3$H]araC trapped under the oil by measuring extracellular space with [$^{14}$C]polyethylene glycol (5 μCi/ml) in separate tubes.

The ability of [SAENTA-$x_2$-fluorescein] *SAENTA-X2-fluorescein* to inhibit influx of nucleoside was assessed in cultured RC2a leukaemic cells by treating the cells for 10 min with graded concentrations of [SAENTA-$x_2$-fluorescein] *SAENTA-X2-fluorescein* (0 to 0.25 μM). Uptake rates of araC (50 μM) were then determined over 20 s at 20° C. as described above.

Figure 4:
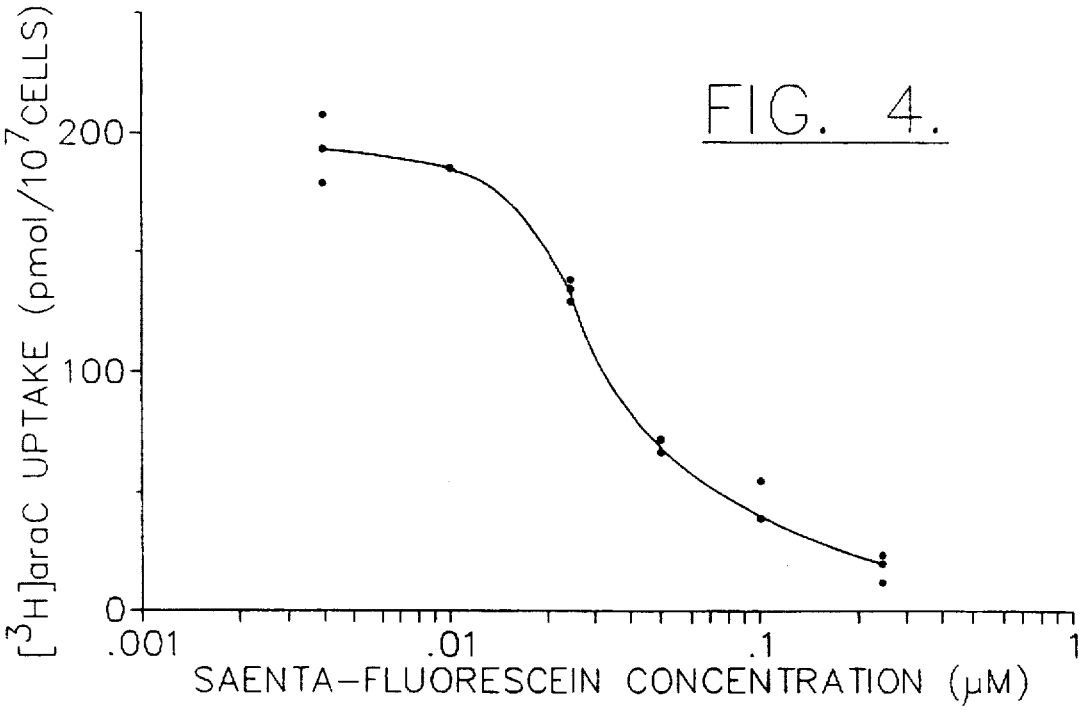
FIG. 4 shows inhibition of araC influx by SAENTA-fluorescein probe.

Influx of [$^3$H]araC (50 μM at 20° C. was inhibited by 90% following exposure of cells for 10 min to 0.25 μM [SAENTA-$x_2$-fluorescein] *SAENTA-X2-fluorescein* as shown in FIG. 4. The $IC_{50}$ for the [SAENTA-$x_2$-fluorescein] *SAENTA-X2-fluorescein* was estimated to be 40 nM.

(b) Inhibition of [$^3$H]NBMPR binding

The binding of [$^3$H]NBMPR to cultured RC2a leukaemic cells was measured in the presence of various concentrations of [SAENTA-$x_2$-fluorescein] *SAENTA-X2-fluorescein* (0–0.86 μM).

Washed RC2a cells ($1\times10^7$ cells/ml) were incubated for 30 min at 37° C. with graded concentrations of [SAENTA-$x_2$-fluorescein] *SAENTA-X2-fluorescein* (0–0.86 μM) and [$^3$H]NBMPR (0.46–8.8 nM total concentration). Determination of the time course for [$^3$H]NBMPR binding (0.46 nM) in the presence of [SAENTA-$x_2$-fluorescein] *SAENTA-X2-fluorescein* (0.1 μM) established that equilibrium was reached by 30 min. The cells were centrifuged through phthalate oil as described above, and bound [$^3$H]NBMPR was measured by liquid scintillation counting (Wiley et al., 1982). The free [$^3$H]NBMPR concentration in the medium above the oil was also measured. Non-specific binding of [$^3$H]NBMPR was measured in parallel incubations of cells treated for 5 min at 37° C. with 5 μM NBMPR before the addition of |$^3$H|NBMPR. Specific binding was calculated by subtracting the amount of non-specific binding (determined in the presence of 5 μM unlabelled NBMPR) from total |$^3$|NBMPR binding in all analyses.

Figure 5:
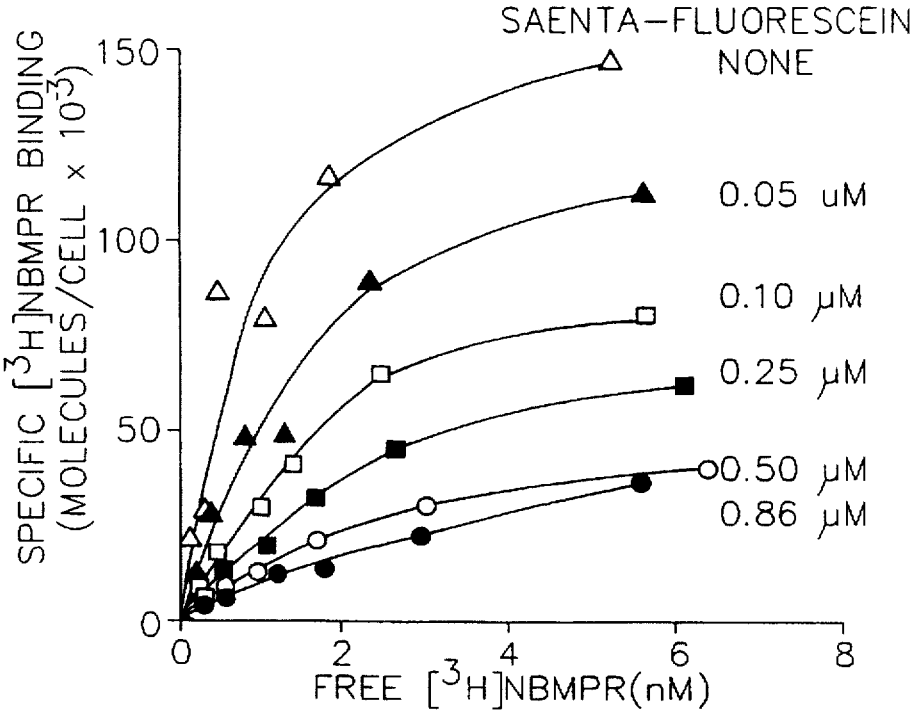
FIG. 5 shows inhibition of NBMPR binding by SAENTA-fluorescein probe.

The fluorescent probe inhibited site-specific |$^3$H|NBMPR binding in a concentration dependent manner with half-maximal inhibition at 50–100 nM (FIG. 5).

(c) Inhibition of |$^3$H| NBMPR binding

The binding of |$^3$H| NBMPR to L1210/B23.1 cells, a clonal line of cultured mouse leukemia L1210 cells which expresses NBMPR binding sites and es nucleoside transporter activity, was measured at 22° under equilibrium conditions in the absence or presence of graded concentrations of SAENTA-fluorescein probes.

Non-specific binding was determined in the presence of 5 μM non-radioactive NBMPR. Mass law (Scatchard) analysis of the binding data was performed with the computer program LIGAND. The $K_d$ value for NBMPR was 0.085±0.015 nM. Replots of $K_d$(app)/$B_{max}$ versus |SAENTA-fluorescein probe| yielded $K_i$ values as in Table 3.

TABLE 3

| Probe | $K_i$ (nM) (mean ± S.D.[n]) |
|---|---|
| 5-(SAENTA-X2)-fluorescein | 17 ± 8 [4] |
| 6-(SAENTA-X2)-fluorescein | 9.9 ± 2.8 [4] |
| 5-(SAENTA-X8)-fluorescein | 0.80 ± 0.21 [4] |
| 6-(SAENTA-X8)-fluorescein | 1.7 ± 0.5 3] |

EXAMPLE 5

Flow cytometry (a) Equilibrium binding of SAENTA—fluorescein probe by flow cytometry RC2a cells grown as in Example 4 were incubated with a range of [SAENTA-$x_2$-fluorescein] *SAENTA-X2-fluorescein* (prepared as in Example 3) concentrations (0–100 nM) at room temperature and the cell-bound fluorescence was analysed by flow cytometry using an EPICS V 741 flow cytometer (Coulter, Hialeah, FL, U.S.A.) fitted with an argon laser. Excitation was at 488 nm and the fluorescence emission was collected between 515 [nM] *nm* and 530 [nM] *nm*.

Forward angle and right angle scatter signals were also collected and used to eliminate fluorescent signals associated with cell debris. [SAENTA-$x_2$-fluorescein] *SAENTA-X2-fluorescein* binding studies with RC2a leukaemic cells ($10^5$ cells per ml in phosphate-buffered saline) were carried out at room temperature. Histograms of relative intensities of cell-associated fluorescence signals were collected under the following conditions (a) prior to any addition of ligand (autofluorescence), (b) following addition of 0 to 100 nM [SAENTA-$x_2$-fluorescein] *SAENTA-X2-fluorescein*, and (c) after a further addition of 1 μM NBMPR or 2 μM dilazep. The mean fluorescence intensity was calculated using integrated signals (i.e. the integral of fluorescence intensity over time taken for each cell to pass through laser beam) from a minimum of 2500 cells. This technique allowed relative fluorescence intensities to be monitored continuously against time to ensure that equilibrium between bound and free [SAENTA-$x_2$-fluorescein] *SAENTA-X2-fluorescein* was reached under each condition. At the lowest ligand concentration equilibrium was reached after 10 min.

(i) Inhibition of binding of SAENTA—fluorescein probe by NBMPR

RC2a leukaemic cells were incubated with 100 nM [SAENTA-$x_2$-fluorescein] *SAENTA-X2-fluorescein* for 10 min at room temperature. NBMPR (1 μM) was then added and the cells incubated for a further 10 min. Histograms of cell bound fluorescence were obtained before and after addition of NBMPR by flow cytometric analysis of approximately 2500 cells. The integrated fluorescent signals generated from individual cells were assigned into 256 channel histograms based on increasing fluorescence intensity.

Figure 6:
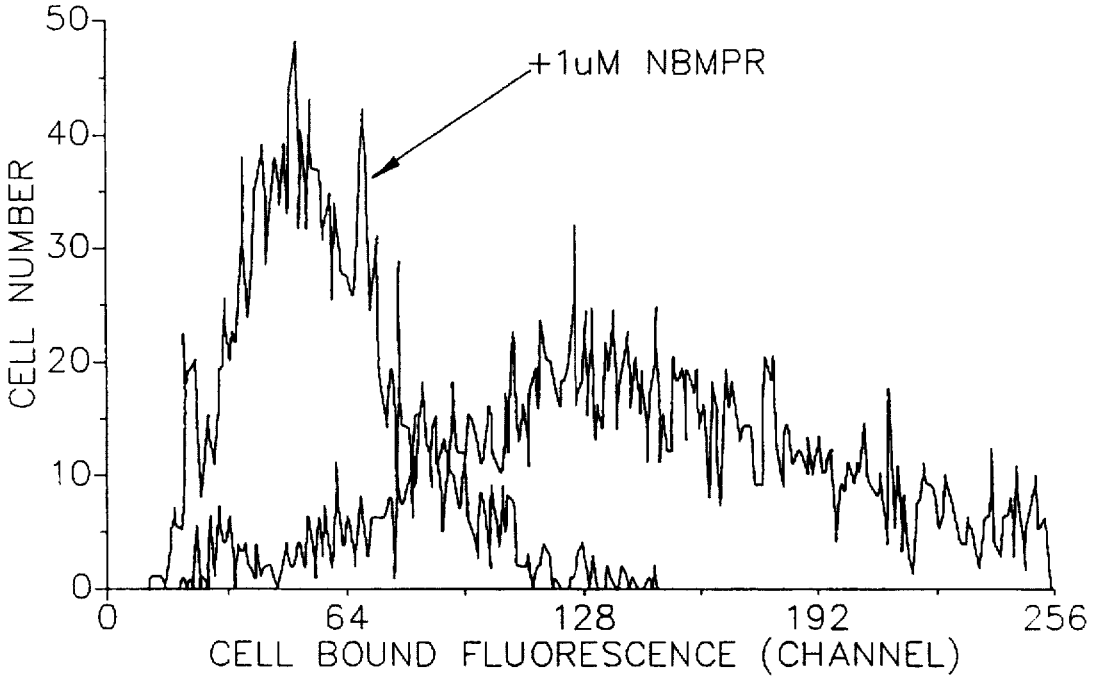
FIG. 6 shows inhibition of binding of SAENTA-fluorescein probe by NBMPR.

The intensity of cell bound fluorescence increased and reached equilibrium values after 10 min of incubation at all ligand concentrations. The histograms of cell bound fluorescence obtained at equilibrium (FIG. 6) show that addition of 1 μM NBMPR reduced the binding of [SAENTA-$x_2$-fluorescein] *SAENTA-X2-fluorescein*.

(ii) Flow cytometry of equilibrium binding of SAENTA—fluorescein probe

RC2a leukaemic cells ($10^5$ cells per ml) were incubated for 10 min at room temperature with a range of [SAENTA-$x_2$-fluorescein] *SAENTA-X2-fluorescein* concentrations (0–100 nM) in the absence (○) or presence (●) of 1 μM NBMPR as shown in FIG. [9] 7. The difference between these two signals represents NBMPR-sensitive [SAENTA-$x_2$-fluorescein] *SAENTA-X2-fluorescein* binding. Cell bound fluorescence has not been corrected for auto-fluorescence which contributes 20–25 channels.

Figure 7:
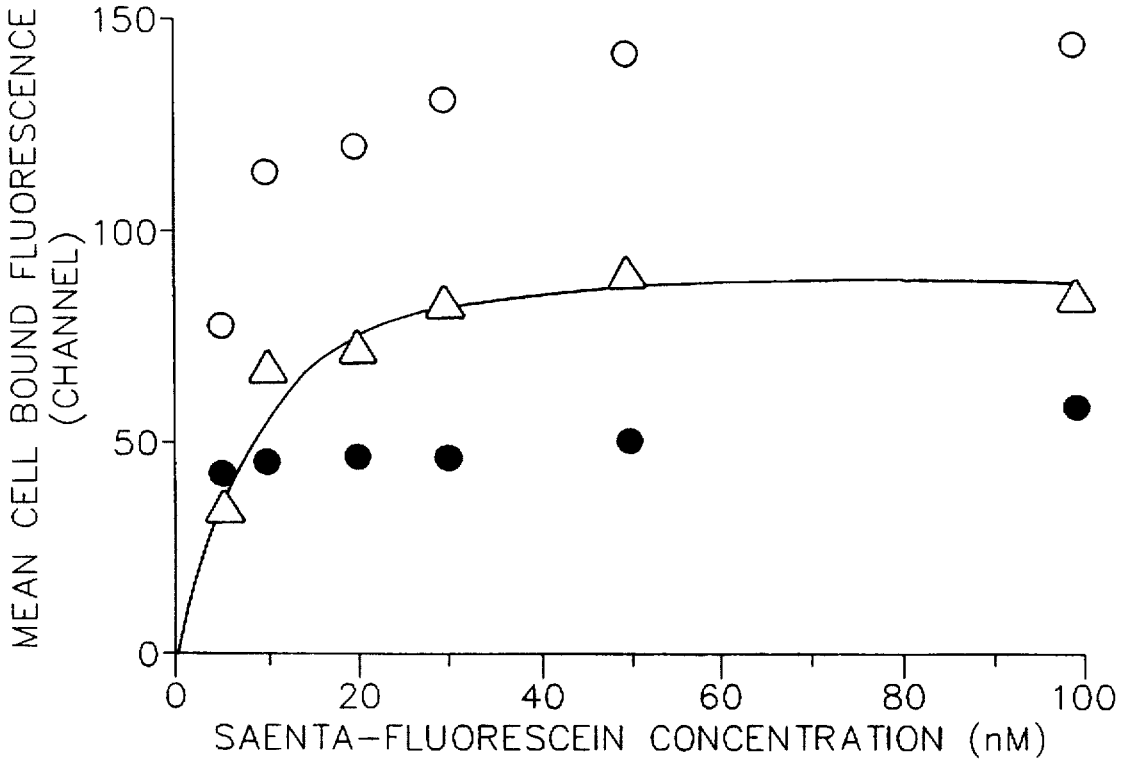
FIG. 7 shows equilibrium binding of SAENTA-fluorescein probe by flow cytometry.

NBMPR-sensitive ligand binding was measured at each [SAENTA-$x_2$-fluorescein] *SAENTA-X2-fluorescein* concentration and plotted against the initial ligand concentration (FIG. 7). Low cell concentrations ($1\times10^5$/ml) were employed in these experiments to minimize depletion of [SAENTA-$x_2$-fluorescein] *SAENTA-X2-fluorescein* from the medium. Under these conditions the concentration of [SAENTA-$x_2$-fluorescein] *SAENTA-X2-fluorescein* giving half-maximal binding was 6.2±1.0 nM (n=3,±1 SD) (FIG. [5] 7).

The specificity of [SAENTA-$x_2$-fluorescein] *SAENTA-X2-fluorescein* binding was further confirmed by measurement sin the presence of dilazep, a potent inhibitor of nucleoside transport structurally, unrelated to NBMPR (Gati and Paterson, 1989 Mol. Pharm., vol. 36, pp. 134–141. Dilazep (2 μM) was found to be as effective as NBMPR (1 μ*M*) in displacing [SAENTA-$x_2$-fluorescein] *SAENTA-X2-fluorescein* binding.

EXAMPLE 6

Specificity of binding of SAENTA-fluorescein probe to es nucleoside transporter

Flow cytometric measurements of binding of [SAENTA-$x_2$-fluorescein] *SAENTA-X2-fluorescein* prepared as in Example 3 was carried out as in Example 4 using two clonal lines of cultured mouse leukemia L 1210 cells, L 1210/B23.1 and L 1210/MA-27.1. L 1210/B23.1 expresses NBMPR binding sites and nucleososide transporter activity whereas L 1210/MA-27.1 cells lack both of these features.

Staining conditions were chosen to minimise non-specific fluorescence signals from L 1210/MA-27.1 cells treated with the nucleoside.

Figure 8B:
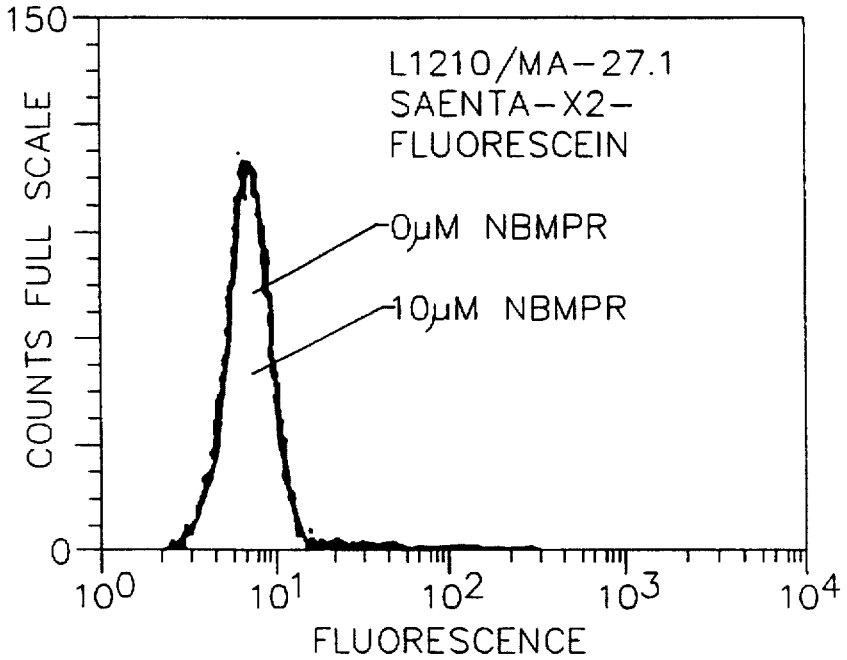
Figure 9A:
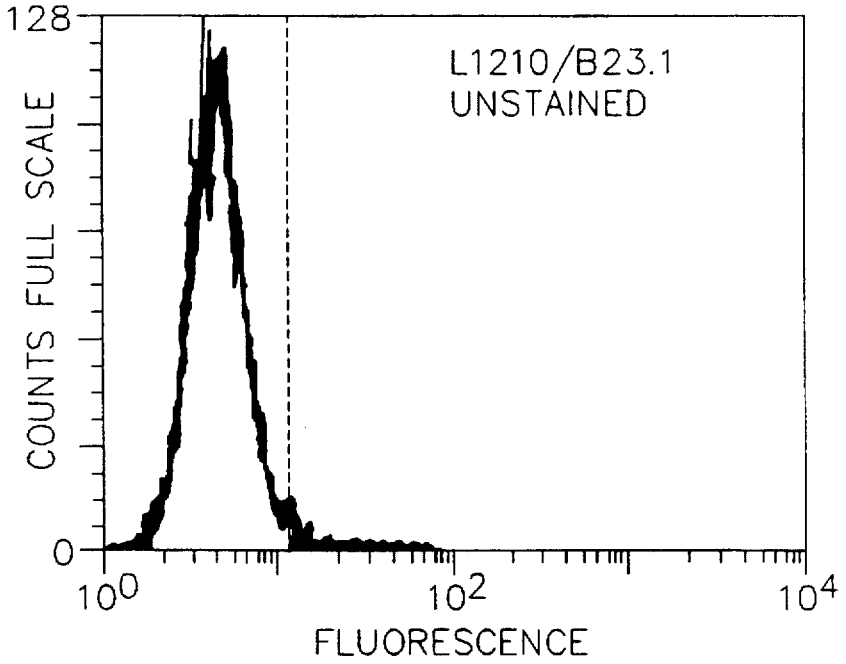
Figure 9B:
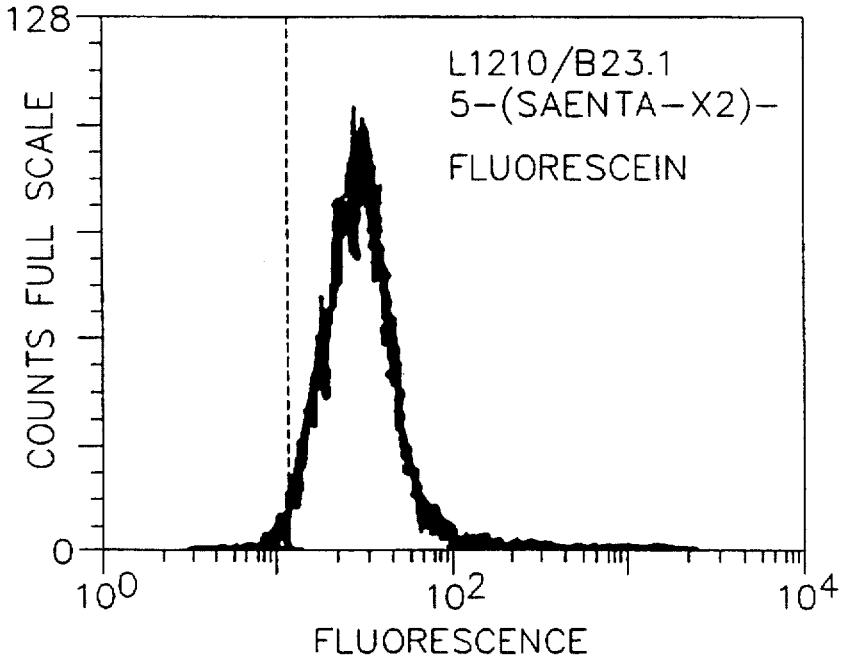
Figure 9C:
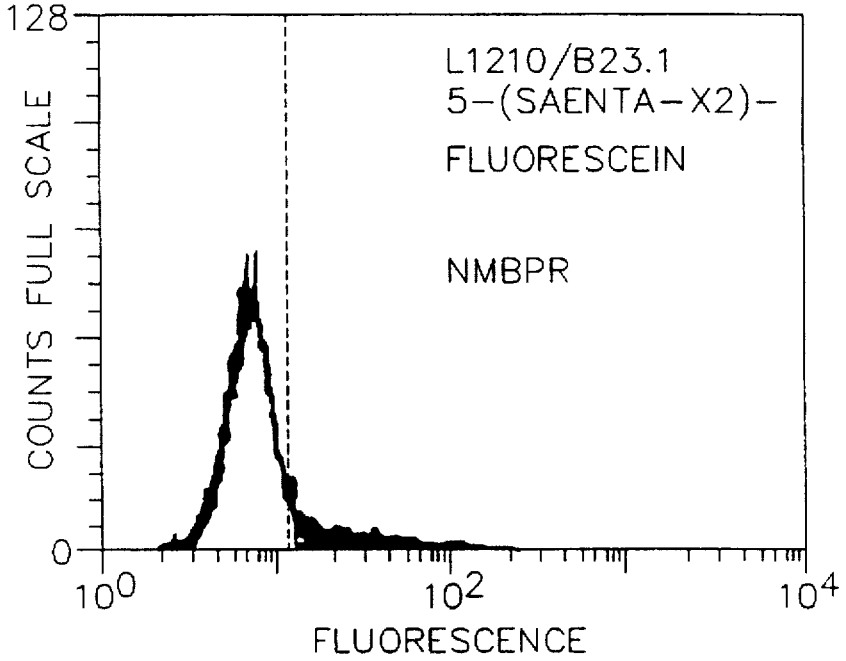
Figure 9D:
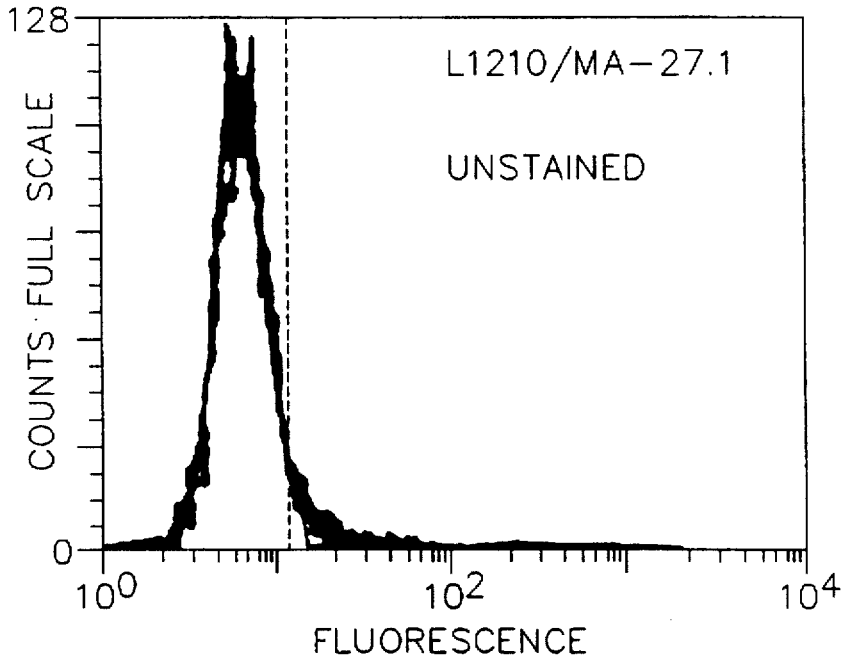
Figure 9E:
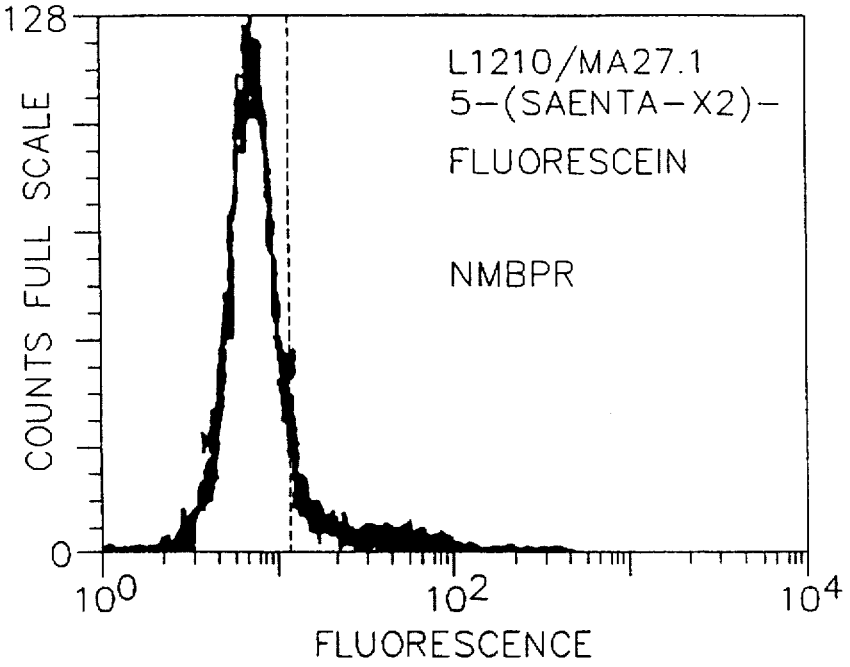
Figure 9F:
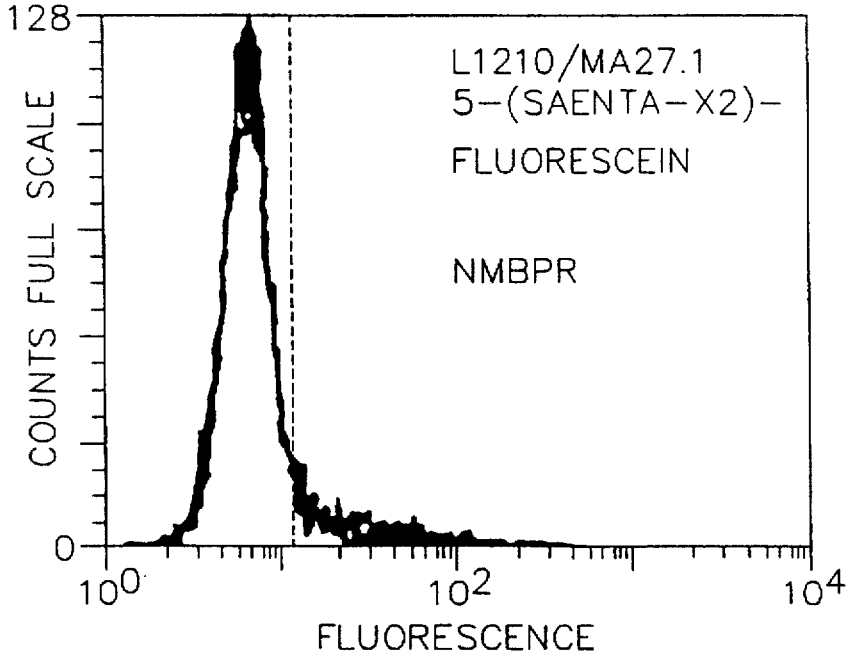

Cells were exposed for 10 min at 4° C. to phosphate-buffered (pH 8.0) salts medium containing 40 nM [5(SAENTA-$x_{x2}$)fluorescein] *5-(SAENTA-X2)-fluorescein* prior to flow cytometric analysis in a BD FACSan instrument; $10^5$ cells were analysed. Cells in replicate assay mixtures were also exposed for 5 min at 22° C. to medium containing 10 μM NBMPR and then for 10 min at 4° C. to medium containing both NBMPR and [5-SAENTA-$x_2$)-fluorescein] *5-(SAENTA-X2)-fluorescein.* The results are shown in FIG. 8, which demonstrates that flow cytometry using [SAENTA-$x_2$-fluorescein] *SAENTA-X2-fluorescein* as a cell stain was able to distinguish clearly between the fluorescence signal from cells showing nucleoside transporter activity (L 1210/B23.1) and that from cells lacking this activity (L 1210/MA-27.1).

EXAMPLE 7

SAENTA-fluorescein probe specific for the es nucleoside transporter (a) Clonal lines of mouse leukemia cells were exposed for 10 min at 4° C. to phosphate buffered (pH 8.0) saline containing 40 mM [5-(SAENTA-$x_2$)-fluorescein] *5-(SAENTA-X2)-fluorescein* (prepared as in Example 3) prior to flow cytometric analysis in a BD FACScan instrument; $10^4$ cells were analysed. Cells in replicate mixtures were also exposed for 5 min at 22° C. to medium containing 10 μM NBMPR and then for 10 min at 4° C. to medium containing both NBMPR and [5-(SAENTA-$x_2$)-fluorescein] *5-(SAENTA-X2)-fluorescein.* L 1210/B23.1 cells express the es nucleoside transport system whereas L 1210/MA-27.1 cells lack that activity.

The results are shown in FIG. 9 which demonstrates that [5-(SAENTA-$x_2$)-fluorescein] *5-(SAENTA-X2)-fluorescein* stained 1210/B23.1 cells and that prior treatment of those cells with 10 μM NBMPR prevented site-specific bonding. The autofluorescence (unstained) of the L 1210/MA27.1 cells is very similar to fluorescence of these cells after staining under standard conditions with [5-(SAENTA-$x_2$)-fluorescein] *5-(SAENTA-X2)-fluorescein* whether or not the cells have been pretreated with NBMPR. Thus, the [5-(Saenta-$x_2$)-fluorescein] *5-(SAENTA-X2)-fluorescein* staining of these cell lines was specific for the es nucleoside transporter system and, as well, the reduction of [5-(SAENTA-$x_2$)-fluorescein] *5-(SAENTA-X2)-fluorescein* binding by prior treatment with NBMPR signified interaction with the es nucleoside transporter.

The SAENTA-fluorescein probes of Table 1 all served as flow cytometer stains for L 1210/B23.1 cells; that staining was markedly reduced by prior treatment with NBMPR. As well, the staining of L 1210/MA27.1 cells (which lack the es nucleoside transporter) by these agents was markedly less than that of L 1210/B23.1 cells.

(b) Concentration-dependence of fluorescent staining of L 1210/23.1 cells by [5-(SAENTA-$x_2$)-fluorescein] *5-(SAENTA-X2)-fluorescein* was measured and the results are set out in Table 4.

Cells in PBS at pH 8.0 were incubated with the listed concentrations of the SAENTA-fluor probe at 4° C. for 40 min prior to flow cytometric analysis.

TABLE 4

| [5-(SAENTA-$x_2$)-] *5-(SAENTA-X2)-* fluorescein (nM) | Fluorescence intensity (mean channel no.) |
|---|---|
| 0* | 298 |
| 5 | 301 |
| 10 | 344 |
| 20 | 372 |
| 40 | 407 |
| 60 | 427 |
| 80 | 429 |
| 160 | 497 |
| 320 | 601 |
| 640 | 691 |
| 1280 | 761 |

*Autofluorescence

Table 4 demonstrates that the fluorescence signal from L 1210/B23.1 cells after exposure to [5-(SAENTA-$x_2$)-fluorescein] *5-(SAENTA-X2)-fluorescein* under these conditions was not maximal, that is, only a fraction of the es nucleoside transporter sites were occupied by [5-(SAENTA-$x_2$)-fluorescein] *5-(SAENTA-X2)-fluorescein* molecules. As the concentration of the probe was increased during the period of cell exposure, cell fluorescence increased, indicating that site occupancy by the probe increased. The data of Table 4 indicate that saturation was reached.

Although only preferred embodiments of the invention have been described, the present invention is not limited to the features of this embodiment, but includes all variations and modifications within the scope of the claims.

We claim:

1. A compound capable of binding to the es nucleoside transporter of animal cells having the general formula:

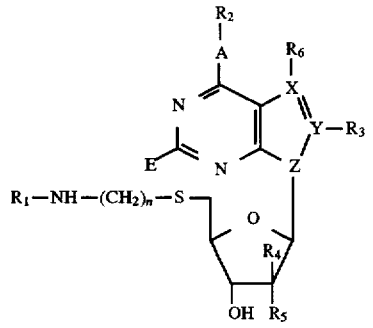

wherein n is 1–12; E is H, halogen, $NH_2$, OH, $OCH_3$, $O(CH_2)_nCH_3$ (where n is 1–12), SH, SR (where R is $CH_3$ or $(CH_2)_nCH_3$ and n is 1 to 12); A is NH, S, O, Se; X is N or C; Y is N or C; Z is N or C; $R_1$ is H or acyl; $R_2$ is C1 to C20 substituted or unsubstituted alkyl or heteroalkyl; substituted or unsubstituted aliphatic carbocycle or heterocycle; substituted or unsubstituted arene or heteroarene, aryl or substituted aryl; heteroaryl or substituted heteroaryl with the proviso that $R_2$ is not methyl; $R_3$ is H, halogen, $NO_2$, $N_3$, SH, SR (where R is $CH_3$ or $(CH_2)_nCH_3$ and n is 1 to 12) *when Y is C and $R_3$ is absent when Y is N*; $R_4$ is H, OH or halogen; $R_5$ is H, OH, halogen, $N_3$, acetal, *or* hemiacetal; and $R_6$ is H, [—C=O—$NH_2$] —*CO—$NH_2$* or —C≡N when X is C and [$R_4$] $R_6$ is [H] *absent* when X is N.

2. A compound in accordance with claim 1 wherein A is NH; $R_2$ is benzyl or substituted benzyl; E is H; X is N; Y is C; Z is N; $R_3$ is H; $R_4$ is H and $R_5$ is OH.

3. A compound in accordance with claim 2 wherein $R_2$ is

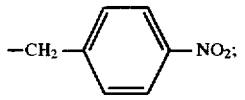

n is 2 and $R_1$ is H.

4. A process for preparing a compound of the general formula:

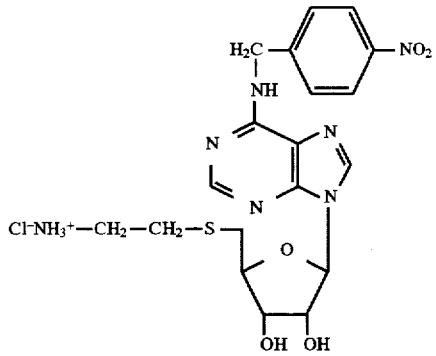

comprising the steps of:

(a) N'1 alkylation and rearrangement of 5'-S-(2-hydroxyethyl)-5'-thioadenosine to give 5'-S-(2-hydroxyethyl-6-N-(4-nitrobenzyl)-5'-thioadenosine;

(b) treatment of the product of step (a) with diethylazodicarboxylate/triphenylphosphine followed by phthalimide to give 5'-S-(2-phthalimidoethyl)-$N^6$-(4-nitrobenzyl)-5'-thioadenosine;

(c) deprotection of the product of step (b) by heating with hydrazine in ethanol to give the phthaloyl hydrazide salt of 5'-S-(2-aminoethyl)-$N^6$-(4-nitrobenzyl)-5'-thioadenosine; and (d) conversion of the product of step (c) to 5'-S-(2-aminoethyl)-6-N-(4-nitrobenzyl)-5'-thioadenosine HCl by ion exchange chromatography on styrene divinyl benzene ($Cl^-$) resin.

5. A probe capable of binding to the es nucleoside transporter of animal cells comprising a compound having the general formula:

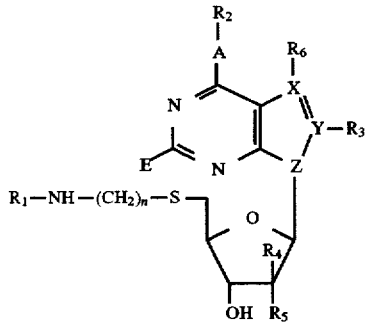

wherein n is 1–12; E is H, halogen, $NH_2$, OH, $OCH_3$, $O(CH_2)_nCH_3$ (where n is 1–12), SH, SR (where R is $CH_3$ or $(CH_2)_nCH_3$ and n is 1 to 12); A is NH, S, O, Se; X is N or C; Y is N or C; Z is N or C; [Z is N or C;] $R_2$ is C1 to C20 substituted or unsubstituted alkyl or heteroalkyl; substituted or unsubstituted aliphatic carbocycle or heterocycle; substituted or unsubstituted arene or heteroarene, aryl or substituted aryl; heteroaryl or substituted heteroaryl with the proviso that $R_2$ is not methyl; $R_3$ is H, halogen, $NO_2$, $N_3$, SH, SR (where R is $CH_3$ or $(CH_2)_nCH_3$ and n is 1 to 12) *when Y is C and $R_3$ is absent when Y is N*; $R_4$ is H, OH or halogen; $R_5$ is H, OH, halogen, $N_3$, acetal, *or* hemiacetal; $R_6$ is H, [—C=O—$NH_2$] —*CO—$NH_2$* or —C≡N when X is C and $R_6$ is [H] *absent* when X is N and $R_1$ is a reporter moiety or a reporter moiety and a linker moiety.

6. A probe in accordance with claim 5 wherein $R_1$ is a reporter moiety and a linker moiety.

7. A probe in accordance with claim 6 wherein said reporter moiety is a fluorescent moiety.

8. A probe in accordance with claim 7 wherein said reporter moiety is a fluorescent moiety selected from the group consisting of fluoresceins, rhodamines, coumarins, eosin, erythrosin, fluorescent phycobili-proteins and fluoresceinated microbeads.

9. A probe in accordance with claim 6 wherein said linker moiety is selected from the group consisting of —CO—, —NHCO$(CH_2)_{n'}$—CO—, 2-amino-5-(3-chloro-triazinyl) or

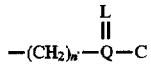

wherein n' is 0 to 12; Q is —C— and L is O or S.

10. A probe in accordance with claim 6 wherein A is NH; $R_2$ is benzyl or substituted benzyl; E is H; X is N; Y is C; Z is N; $R_3$ is H; $R_4$ is H; and $R_5$ is OH.

11. A probe in accordance with claim 10 wherein $R_2$ is

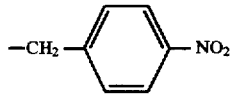

and n is 2.

12. A probe in accordance with claim 11 wherein said reporter moiety is a fluorescent moiety and said linker moiety is selected from the group consisting of: —CO—, —NHCO$(CH_2)_{n'}$—CO—, 2-amino-5-(3-chloro-triazinyl) or

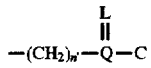

wherein n' is 0 to 12; Q is C and L is O or S.

13. A probe in accordance with claim 12 wherein said fluorescent moiety is 5-fluorescein or 6-fluorescein and said linker moiety is —CO—, —NHCS, —NHCO$(CH_2)_5$—CO—, or 2-amino-5-(3-chloro-triazinyl)—.

14. A probe in accordance with claim 13 wherein said fluorescent moiety is 5-fluorescein and said linker moiety is —NHCS—.

15. A probe in accordance with claim 5 wherein said reporter moiety is a radioactive moiety.

16. A probe in accordance with claim 15 wherein said radioactive moiety is labelled with a γ-emitting isotope selected from the group consisting of $^{123}I$, $^{125}I$ and $^{99m}Tc$.

17. A probe in accordance with claim 5 wherein said reporter moiety is a moiety which binds specifically with a reporter-specific moiety, the reporter moiety/reporter-specific moiety binding pair being selected from the group consisting of avidin/biotin, avidin/iminobiotin, streptavidin/biotin and antigen/antibody.

18. A probe in accordance with claim 17 wherein said reporter moiety is fluorescein and said binding pair is fluorescein/antifluorescein antibody.

19. A method of determining es nucleoside transporter sites of animal cells comprising the steps of:

(a) contacting a suitable preparation of said cells with a probe in accordance with claim 5 to permit binding of said probe to said sites; and (b) determining said reporter moiety of said probe.

20. A method of determining es nucleoside transporter sites of animal cells comprising the steps of:

(a) contacting said cells with a probe in accordance with claim 5 to permit binding of said probe to said sites;

(b) contacting said cells treated as in (a) with a reporter-specific moiety capable of binding to the reporter moiety of said probe; and (c) determining said reporter-specific moiety.

21. A method in accordance with claim 19 wherein said animal cells are human cells.

22. A pharmaceutical composition in dosage unit form suitable for inhibiting es nucleoside transporter activity in animal cells and tissues comprising a compound in accordance with claim 1 or a pharmaceutically acceptable salt thereof in an amount effective to inhibit as nucleoside transporter activity in admixture with a suitable pharmaceutical carrier.

23. A pharmaceutical composition in accordance with claim 22 suitable for inhibiting es nucleoside transporter activity in human cells and tissues.

24. A kit for determining es nucleoside transporter sites of animal cells comprising:

(a) a probe in accordance with claim 5;

(b) reagent means for determining the reporter moiety of said probe, said probe and reagent means each being present in amounts effective to perform the determination.

25. A kit in accordance with claim 24 wherein said animal cells are human cells.

26. A compound in accordance with claim 1 linked to a macromolecular carrier.

27. A compound in accordance with claim 1 linked to agarose.

28. A method for inhibiting es transport activity in an animal by administering an es transporter activity inhibiting amount of the pharmaceutical composition of claim 22 or 23 to said animal.

* * * * *